United States Patent
Krammer et al.

(10) Patent No.: US 12,329,800 B2
(45) Date of Patent: Jun. 17, 2025

(54) ANNEXIN-COATED PARTICLES

(71) Applicant: Deutsches Krebsforschungszentrum Stiftung des öffentlichen Rechts, Heidelberg (DE)

(72) Inventors: Peter Krammer, Heidelberg (DE); Heiko Weyd, Heidelberg (DE); Kevin Bode, Heidelberg (DE)

(73) Assignee: Deutsches Krebsforschungszentrum Stiftung des Öffentlichen Rechts, Heidelberg (DE)

( * ) Notice: Subject to any disclaimer, the term of this patent is extended or adjusted under 35 U.S.C. 154(b) by 783 days.

(21) Appl. No.: 17/429,532

(22) PCT Filed: Feb. 6, 2020

(86) PCT No.: PCT/EP2020/053007
§ 371 (c)(1),
(2) Date: Aug. 9, 2021

(87) PCT Pub. No.: WO2020/161247
PCT Pub. Date: Aug. 13, 2020

(65) Prior Publication Data
US 2022/0152149 A1 May 19, 2022

(30) Foreign Application Priority Data
Feb. 8, 2019 (EP) ................. 19156258

(51) Int. Cl.
A61K 38/00 (2006.01)
A61K 9/16 (2006.01)
A61K 38/17 (2006.01)
A61K 47/54 (2017.01)
A61P 37/06 (2006.01)

(52) U.S. Cl.
CPC .......... *A61K 38/1709* (2013.01); *A61K 9/167* (2013.01); *A61K 47/544* (2017.08); *A61P 37/06* (2018.01)

(58) Field of Classification Search
CPC .. A61K 38/1709; A61K 9/167; A61K 47/544; A61K 9/5052; A61K 9/127; A61K 9/1271; A61K 9/1277; A61K 38/47–64; A61K 38/6901; A61K 38/6911; A61K 38/6921
See application file for complete search history.

(56) References Cited

U.S. PATENT DOCUMENTS

| 2006/0009381 | A1 | 1/2006 | Reutelingsperger |
| 2010/0109212 | A1 | 5/2010 | Leonard |
| 2011/0014270 | A1* | 1/2011 | Holers ............... A61K 9/127 530/389.1 |
| 2012/0115771 | A1 | 5/2012 | Cordeiro et al. |
| 2018/0275124 | A1 | 9/2018 | Krammer et al. |

FOREIGN PATENT DOCUMENTS

| JP | 2007-537432 A | 12/2007 |
| JP | 2012521977 A | 9/2012 |
| WO | 20100109212 A2 | 9/2010 |
| WO | 2005114192 | 12/2015 |
| WO | 2016179430 | 11/2016 |

OTHER PUBLICATIONS

Davis et al. Topical Delivery of Avastin to the Posterior Segment of the Eye In Vivo Using Annexin A5-associated Liposomes. small. 2014, vol. 10, No. 8, pp. 1575-1584. (Year: 2014).*
Kohler et al. Annexin V Interaction with Phosphatidylserine-Containing Vesicles at Low and Neutral pH. Biochemistry. 1997, vol. 36, No. 26, pp. 8189-8194. (Year: 1997).*
International Search Report, dated May 13, 2020, from corresponding International Application No. PCT/EP2020/053007.
Written Opinion of the International Searching Authority, dated May 13, 2020, from corresponding International Application No. PCT/EP2020/053007.
Ong, Sandy Gim Ming et al. "Evaluation of Extrusion Technique for Nanosizing Liposomes." Pharmaceutics, 8 (36):1-12, Dec. 21, 2016.
Perretti, Mauro & Gavins, Felicity N. E. "Annexin 1: An Endogenous Anti-Inflammatory Protein." News Physiol Sci 18:60-64, (Year: 2003).

* cited by examiner

*Primary Examiner* — Jeanette M Lieb
(74) *Attorney, Agent, or Firm* — SALIWANCHIK, LLOYD & EISENSCHENK

(57) ABSTRACT

The present invention relates to an annexin-coated particle, comprising a negatively charged phospholipid and an annexin non-covalently coupled thereto. The present invention further relates to a composition comprising an annexin-coated particle. Furthermore, the present invention relates to a product for use in a method of preventing or treating a disease selected from a chronic inflammatory disease, an autoimmune disease, an allergy, and a cancer, said product comprising an annexin-coated particle, and/or a composition. The present invention further relates to a method of preparing an annexin-coated particle.

14 Claims, 21 Drawing Sheets

Figure 3, continued
c
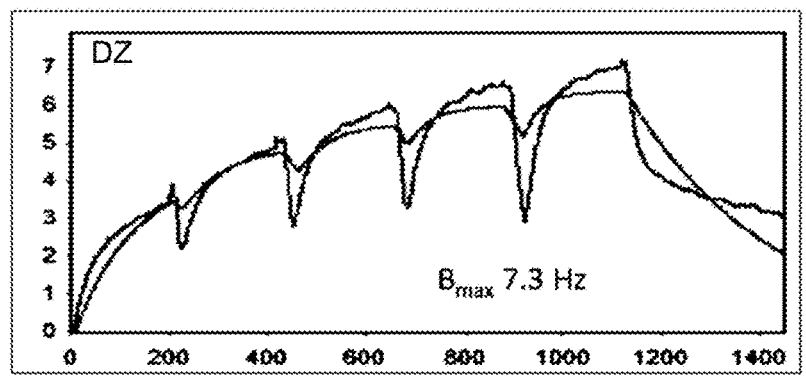
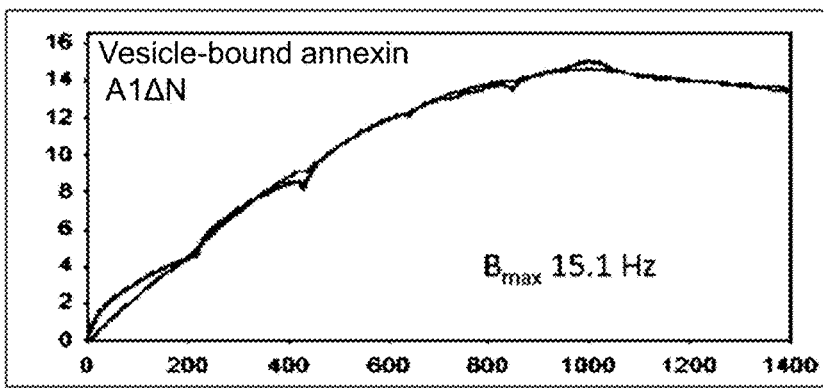
d
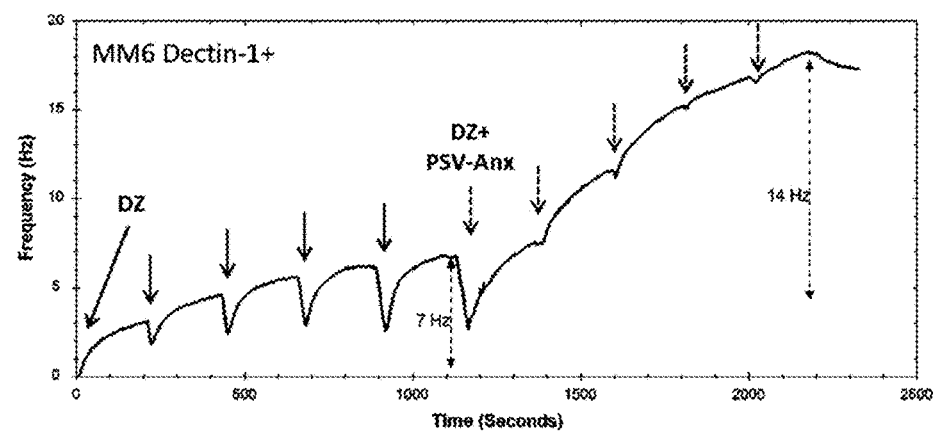
e
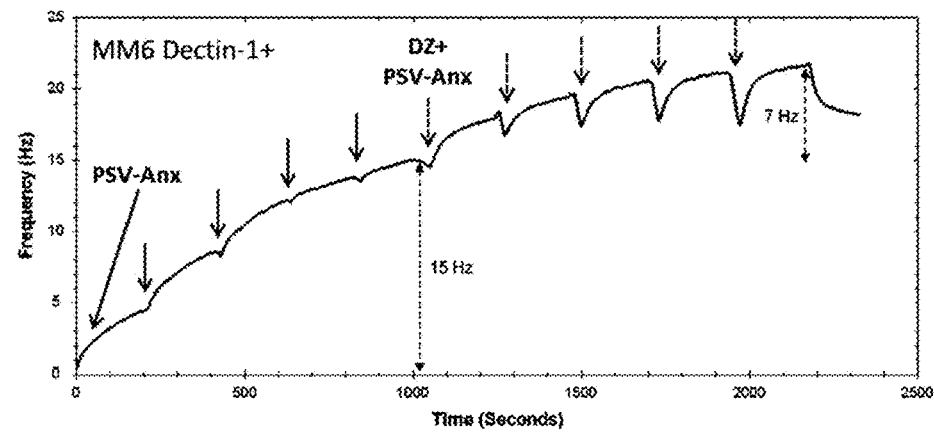

Figure 4, continued
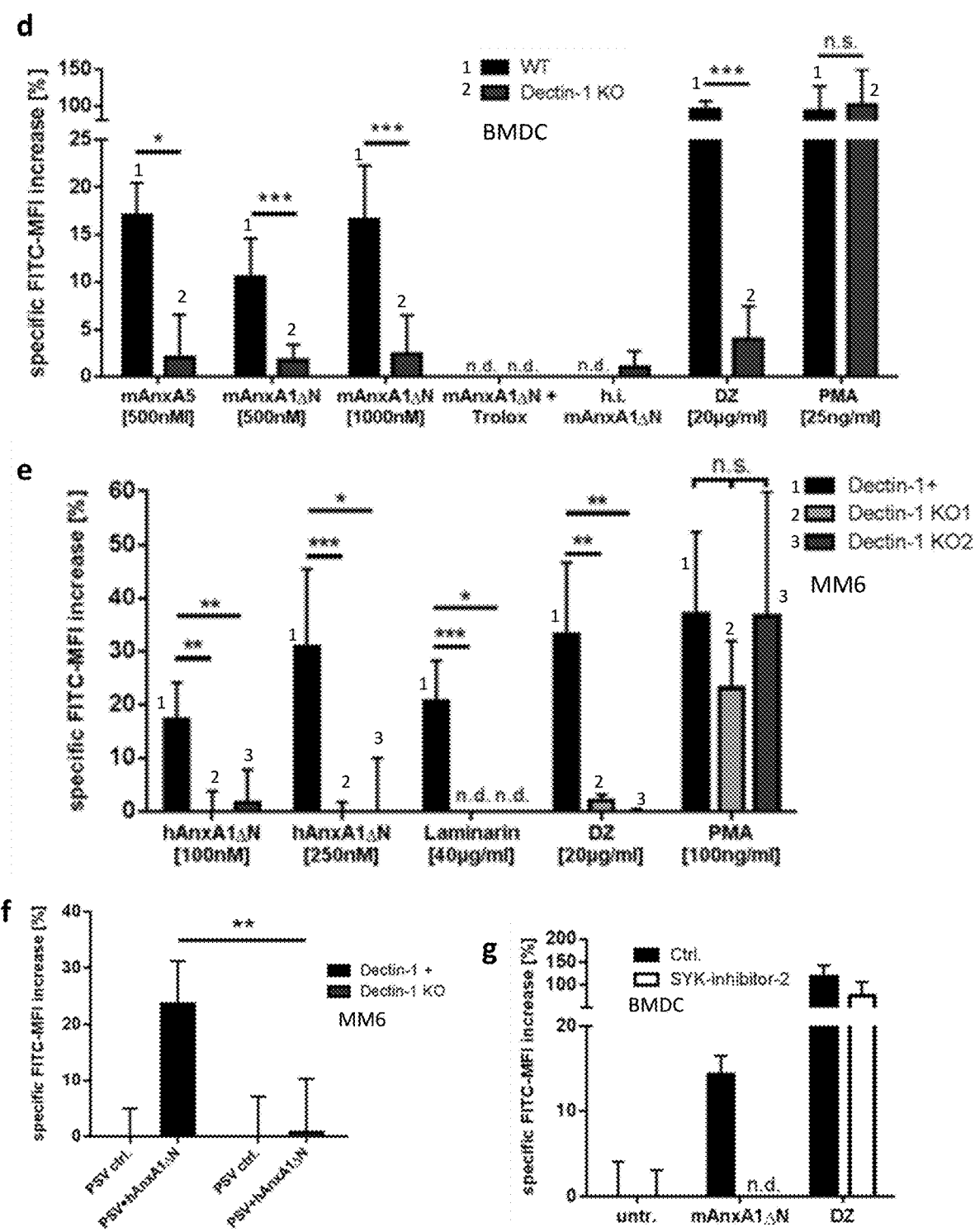

Figure 5, continued
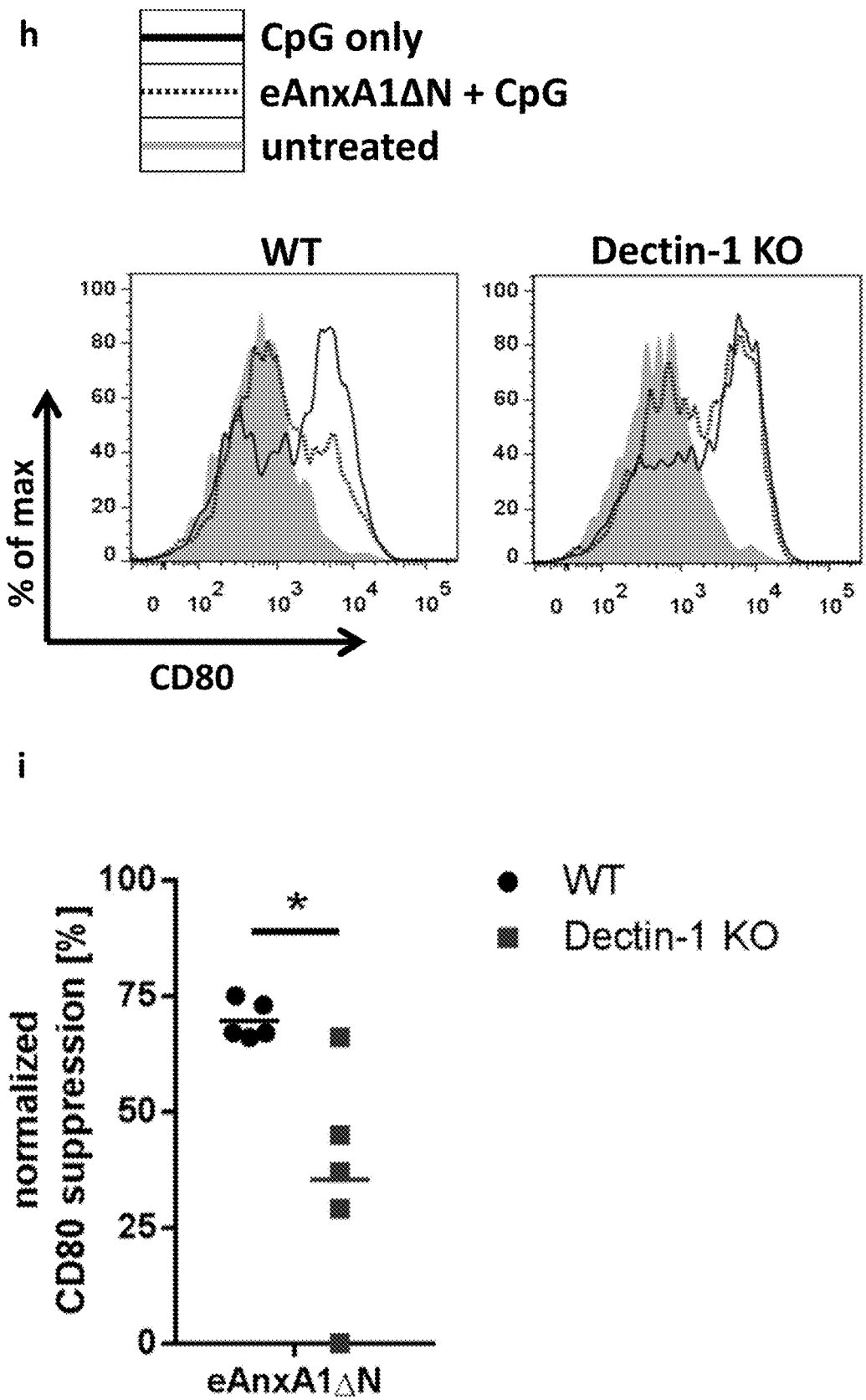

a b c d e f

Figure 6, continued
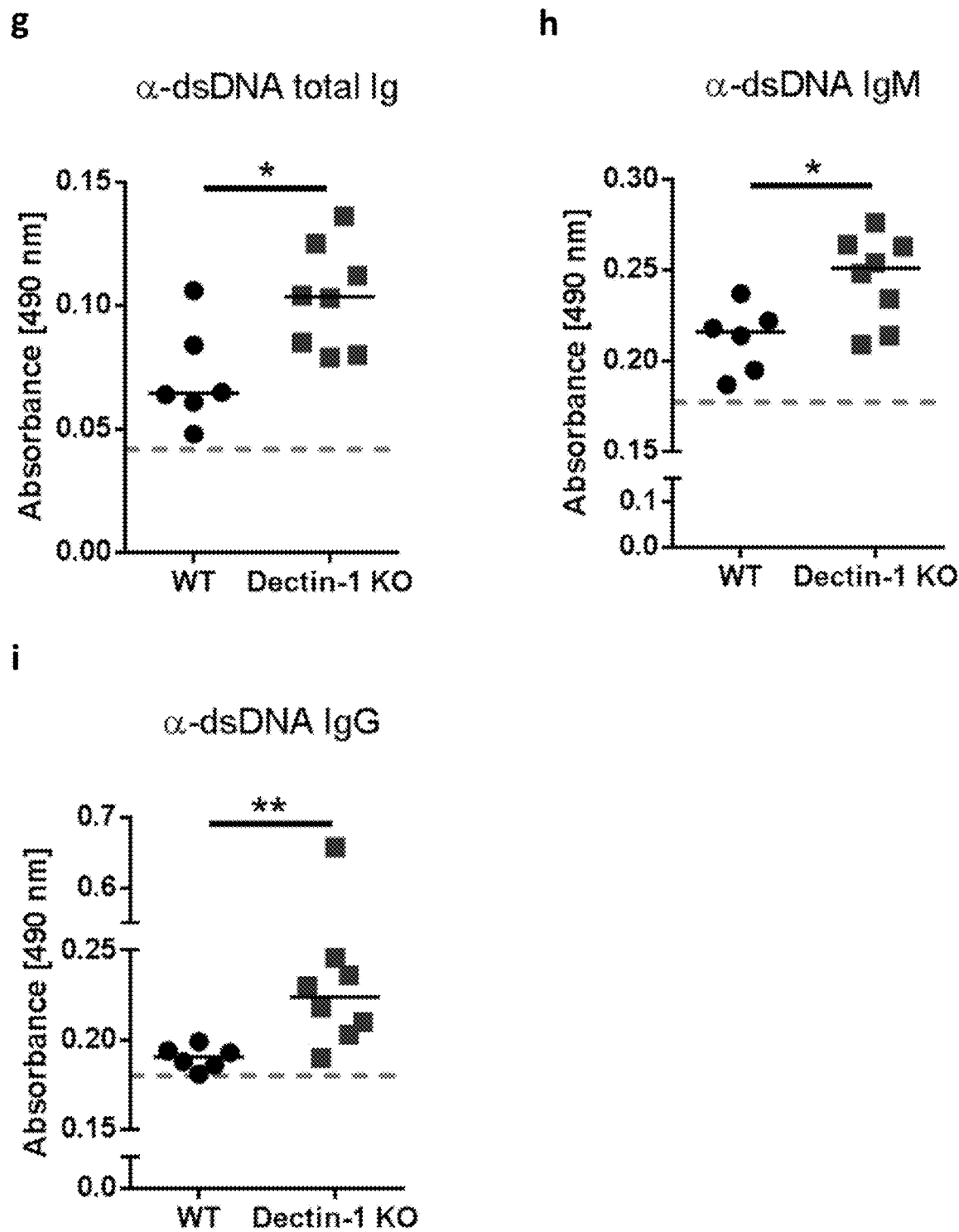

Figure 7, continued
d AnxA5-Dectin-1 Fc vs. Fc control
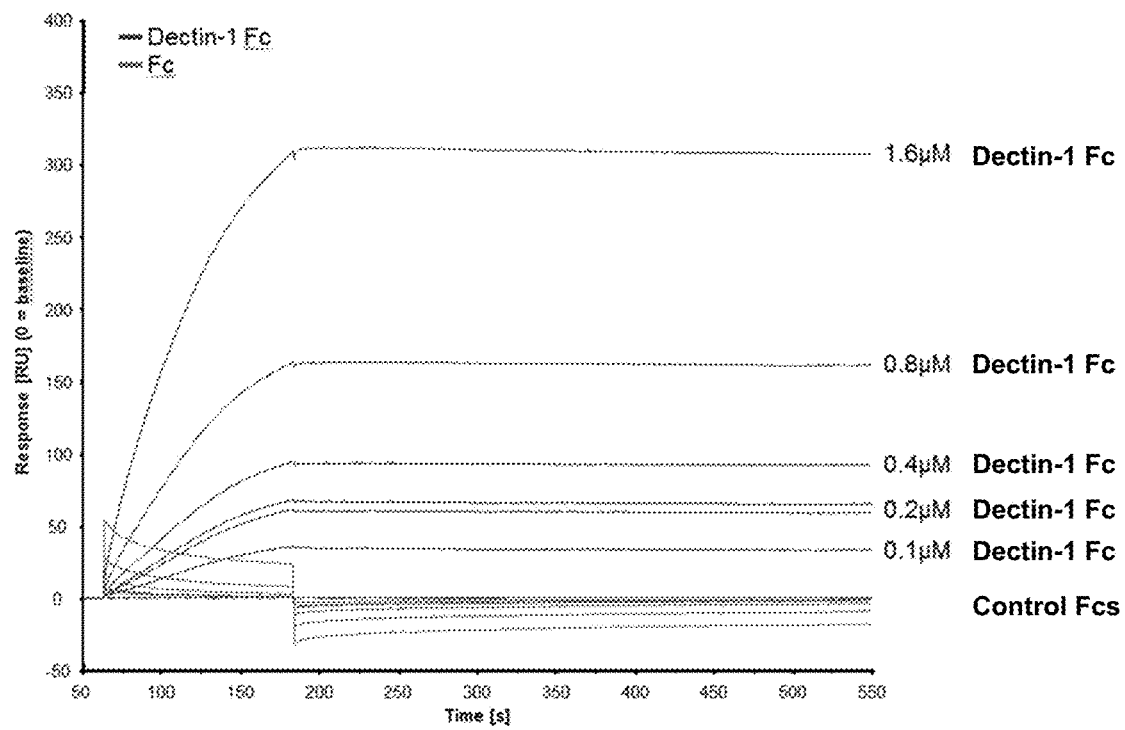

Figure 7, continued
e  AnxA13-Dectin-1 Fc vs. Fc control
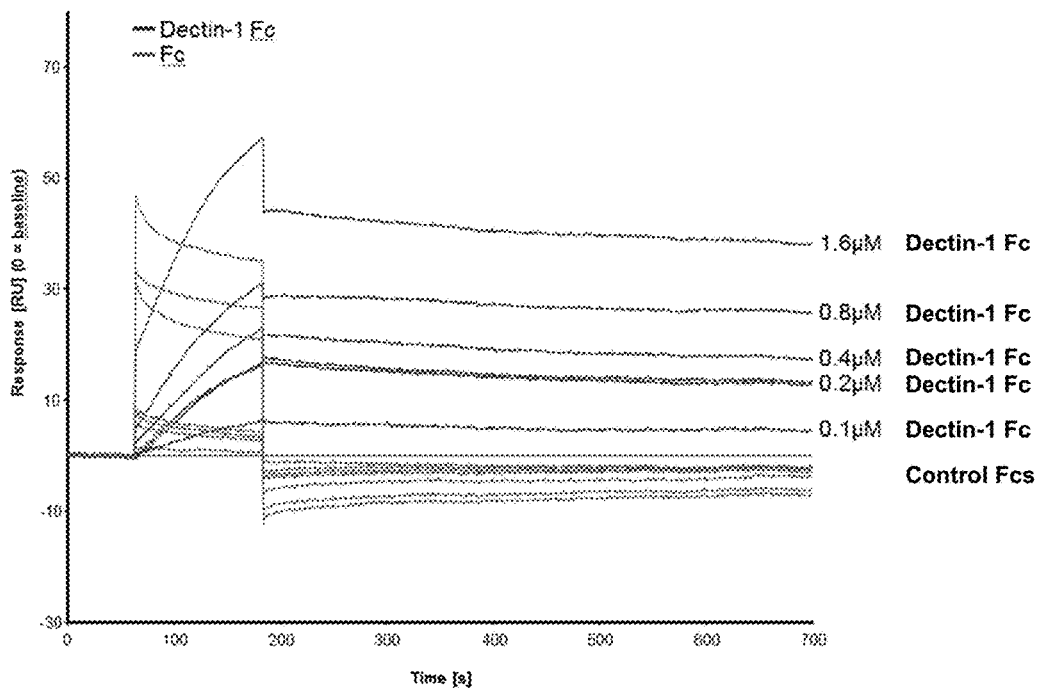
f  AnxA1ΔN-Dectin-1 Fc vs. Fc control
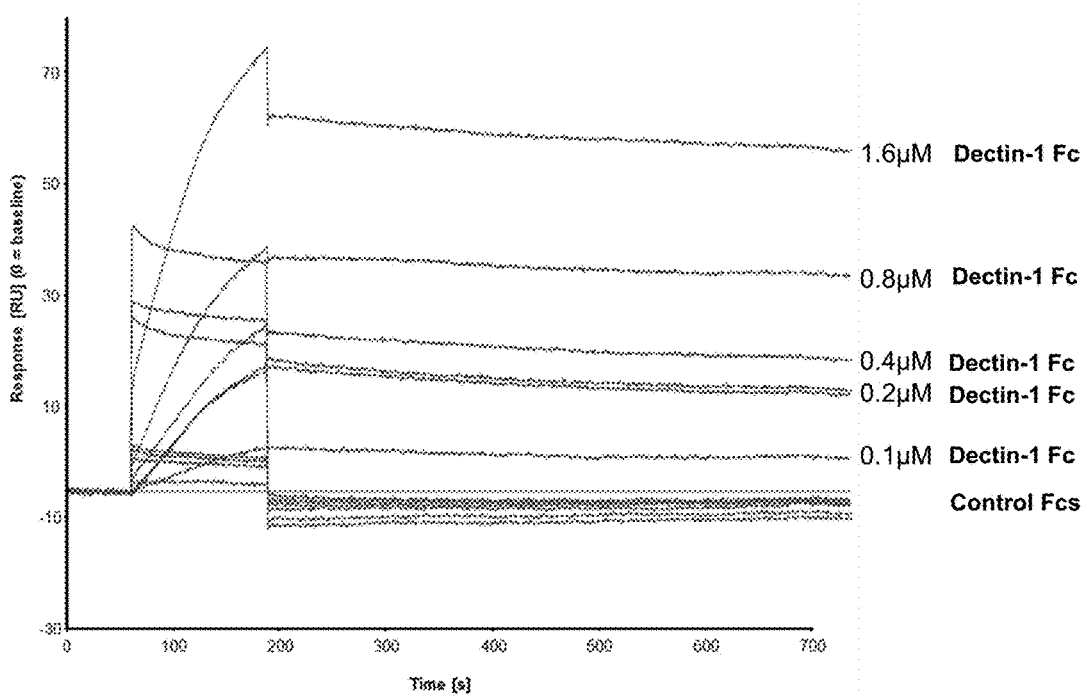

Figure 7, continued
g    AnxA1-Dectin-1 Fc vs. MICL Fc
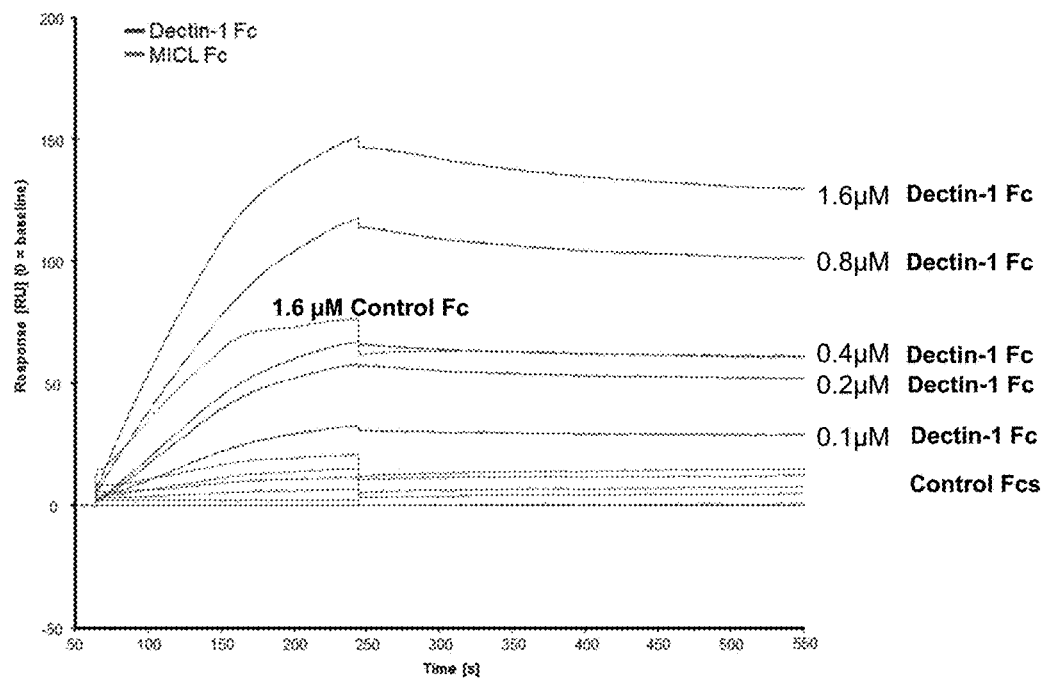
h    AnxA1-Dectin-1 Fc vs. SIGNR3 Fc
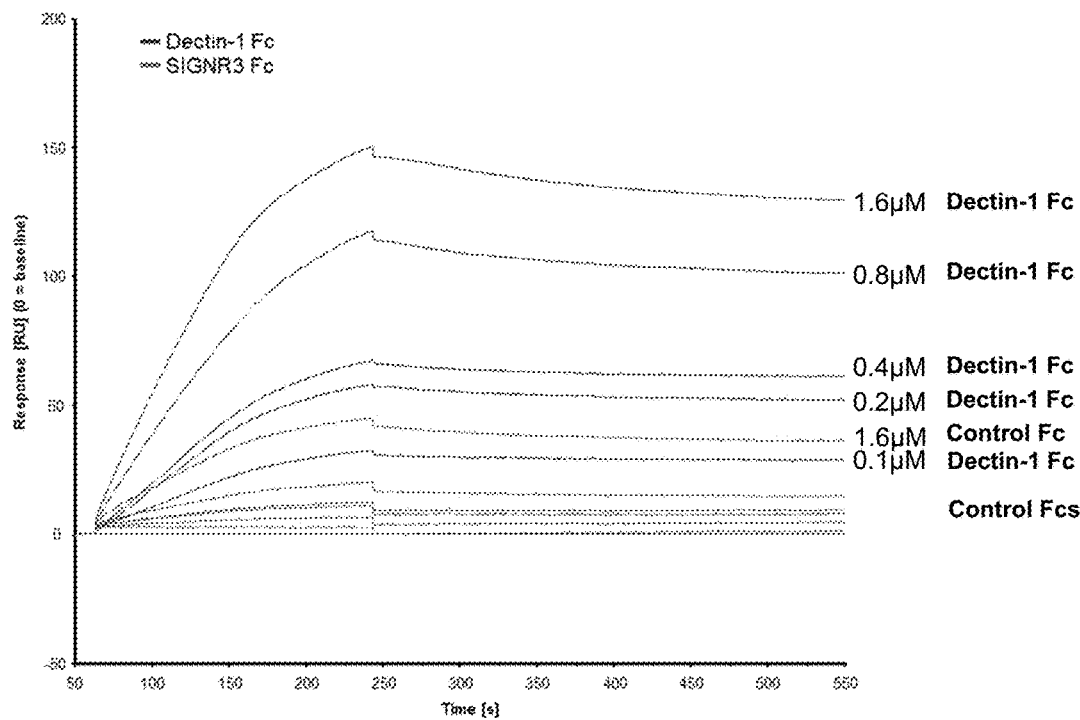

ANNEXIN-COATED PARTICLES

FIELD OF THE INVENTION

The present invention relates to an annexin-coated particle, comprising a negatively charged phospholipid and an annexin non-covalently coupled thereto. The present invention further relates to a composition comprising an annexin-coated particle. Furthermore, the present invention relates to a product for use in a method of preventing or treating a disease selected from a chronic inflammatory disease, an autoimmune disease, an allergy, and a cancer, said product comprising an annexin-coated particle, and/or a composition. The present invention further relates to a method of preparing an annexin-coated particle.

BACKGROUND OF THE INVENTION

Removal of apoptotic cells (ACs) is closely associated with the induction of immunological self-tolerance. Each day, billions of ACs are phagocytosed by antigen-presenting cells such as dendritic cells (DCs) and actively modulate the immune response. Following engulfment of ACs, DCs acquire a tolerogenic phenotype characterized by low expression of co-stimulatory surface molecules and inflammatory cytokines and resistance to activation [1]. Such tolerogenic DCs process and present AC-derived self-antigens to naïve T-cells and induce T-cell tolerance [2].

Early ACs expose several members of the annexin protein family on their surface which serve as inhibitory signals to DCs facilitating the development of peripheral tolerance [3],[4]. Annexins are a family of cytosolic proteins which bind to negatively charged phospholipids such as phosphatidylserine in a calcium dependent manner. Lipid binding is mediated by the C-terminal core domain highly conserved among all annexin family members, and peptides corresponding to the AnxA1 N-terminus were shown to bind to members of the N-formyl peptide receptor (FPR) family, resulting in a reduction of neutrophil transmigration in several models of acute and chronic inflammation [5].

Structurally, annexins are comprised of an evolutionary well conserved annexin core domain and a unique N-terminus. The early exposure of the cytosolic protein annexin A1 (AnxA1) was identified as a tolerogenic signal on the surface of ACs [3]. Extracellular immune regulatory functions have been described most prominently for annexin A1 and have been attributed to its N-terminus binding to the N-formyl peptide receptor (FPR) family. However, the tolerogenic function mediated by the conserved annexin core domain is independent of FPRs [4].

Furthermore, annexin binds to Dectin-1 (also known as CLEC7A) which belongs to the C-type lectin receptor (CLR) superfamily expressed on DCs and other immune cells [6]. It serves as pattern-recognition receptor with high affinity to β-1,3-linked glucans (β-glucans) present in cell walls of fungal and bacterial species. Dectin-1 is involved in activation of immune reactions following microbial and fungal infections. Signaling of Dectin-1 mainly depends on the hemi-ITAM in its cytoplasmic region, activating signaling pathways through spleen tyrosine kinase (SYK), Raf-1 and Card-9. In addition, Dectin-1 stimulation by β-glucans leads to the production of reactive oxygen species (ROS) by activating NADPH oxidase-2 (NOX-2). Stimulation of Dectin-1 can initiate anti-inflammatory and tolerogenic responses, limiting the induction of type 1 diabetes and allergic immune reactions.

Annexins and annexin-preparations are currently under investigation for their therapeutic potential in diseases like chronic inflammatory and autoimmune diseases, allergy and cancer vaccination (Therannex, DKFZ; Trio Medicines Ltd, UK) as well as cardiovascular diseases (Annexin Pharmaceuticals, Sweden). Common to most of these therapeutical annexin applications is the use of a soluble annexin-preparation. However, in addition to desired binding to specific receptor(s), soluble annexin is known to bind to negatively charged phospholipids such as phosphatidylserine (PS). Thus, high background binding and off-target effects are often observed for soluble annexin preparations when administered in vivo, due to PS-expression on various cellular and vascular surfaces [7], [8]. Soluble annexin typically binds randomly to membranes comprising negatively charged phospholipids and does not selectively bind to target receptors on target cells These off-target effects reduce the effective annexin concentration drastically, prompting the administration of very high annexin doses. Moreover, high annexin dosages often lead to undesired side effects, e.g. induction of vascular leakage by reduced coagulation.

WO 2007/069895 relates to compositions and methods for treating and diagnosing a subject by delivering compounds to a specified target using novel annexins, variants of annexins, and derivatives thereof.

WO 2016/113022 describes that annexins are related to specific receptors, which could be stimulated or blocked by either binding of one of the annexins or fragments thereof or an antibody against this receptor. Thus, annexins and/or functional fragments thereof and/or fusion proteins comprising an annexin or functional fragments thereof are noted to be of use to modulate the immune system. WO2016/113022 is silent about any means to reduce off-target binding of annexin preparations.

WO 2005/027965 discloses annexins and anti-annexin antibodies and their uses, such as for detecting apoptosis and for the production of pharmaceutical compositions for the diagnosis and/or treatment of cancer, autoimmune diseases, cardiovascular and/or vascular diseases. WO 2005/027965 does not relate to reducing off-target binding of annexin.

WO 2001/072277 discloses a phospholipid vesicle for producing an immune response, the phospholipid vesicle having an antigen or a polynucleic acid coding for an antigen therein. WO 2001/072277 does not relate to annexin-coated particles having reduced off-target binding properties.

Gamier et al. [9] disclose liposomes functionalized with PEGylated lipids which are covalently linked to annexin A5 proteins as cell-targeting elements. Gamier et al. does not relate to a means of reducing off-target binding of annexin.

Accordingly, there is a need to provide an annexin preparation which exhibits lower off-target binding and thus has a higher effective annexin concentration for binding to target cells than soluble annexin.

It is therefore an object of the present invention to provide an annexin preparation and/or a product that has the therapeutic effectivity of annexin and has reduced side effects over other annexin preparations such as soluble annexin preparations. Accordingly, the present invention aims at providing an improved annexin preparation exhibiting reduced off-target binding, and a method of preparing said annexin preparation. Furthermore, it is an object of the present invention to employ these preparations and/or products in the development of new and effective therapies, particularly in the treatment of a disease selected from chronic inflammatory diseases, autoimmune diseases, allergies, and cancer. Furthermore, it is an object of the present invention to provide a means for inducing a tolerogenic response in target cells such as dendritic cells. Other objects and aspects of the present invention will become apparent to the person of skill upon reading the following description of the invention.

SUMMARY OF THE INVENTION

In the following, the elements of the invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine two or more of the explicitly described embodiments or which combine the one or more of the explicitly described embodiments with any number of the disclosed and/or preferred elements. Furthermore, any permutations and combinations of all described elements in this application should be considered disclosed by the description of the present application unless the context indicates otherwise.

In a first aspect, the invention relates to an annexin-coated particle, comprising a negatively charged phospholipid and an annexin non-covalently coupled thereto.

In one embodiment, said annexin is any member of the group of annexins, preferably any of annexin A1, annexin A5, and annexin A13, more preferably annexin A1 or annexin A5, and/or is a receptor-binding annexin core domain or a fragment thereof, preferably any of an annexin A1, A5, and A13 core domain or a fragment thereof, more preferably a human annexin A1 or A5 core domain or a fragment thereof.

In one embodiment, said negatively charged phospholipid is any of phosphatidylserine, phosphatidylglycerol, phosphatidic acid, phosphatidylinositol, phosphatidylinositol phosphate, phosphatidylinositol biphosphate, phosphatidylinositol triphosphate, 1,2-dimyristoyl-sn-glycero-3-phosphoglycerol sodium salt (DMPG), 1,2-dimyristoyl-sn-glycero-3-phospho-L-serine sodium salt (DMPS), and 1,2-dimyristoyl-sn-glycero-3-phosphate monosodium salt.

In one embodiment, said particle further comprises any phospholipid selected from phosphatidylcholine, phosphatidylethanolamine, sphingomyelin, and combinations thereof.

In one embodiment, said particle comprises phosphatidylserine, phosphatidylcholine, and phosphatidylethanolamine.

In one embodiment, said particle comprises phosphatidylserine in a range of from 0.5% to 100%, phosphatidylcholine in a range of from 0% to 99.5%, and phosphatidylethanolamine in a range of from 0% to 20%, wherein said percentages are molar percentages with regard to the total phospholipid content, wherein the sum of the molar percentages of phosphatidylserine, phosphatidylcholine, and phosphatidylethanolamine does not exceed 100%.

In one embodiment, said particle incorporates said negatively charged phospholipid in a particle main body and/or is covered with said negatively charged phospholipid.

In one embodiment, said particle further comprises cholesterol, PEG, a therapeutic agent other than annexin, and/or an antigen.

In one embodiment, said particle is a nano- or microparticle.

In one embodiment, said particle has a mean diameter in a range of from 20 nm to 1000 nm, preferably ≤400 nm.

In one embodiment, said particle is selected from a lipid vesicle, a micelle, a solid-lipid particle, a polymeric particle, a polysaccharide particle such as an agarose bead, an iron oxide particle, a dendrimer, a viral-based particle, a DNA-based particle, a modified cell, an artificial cell, and a carbon nanotube.

In one embodiment, said particle is a lipid vesicle, preferably a unilamellar or multilamellar lipid vesicle.

In one embodiment, said particle is capable of binding to a receptor on a target cell, preferably to any of Dectin-1, DC-SIGN, Lrp1, Complement receptor 3 (ITGAM, CD11b), a formyl peptide receptor (FPR), and a lipoxin receptor.

In one embodiment, said particle is capable of binding to Dectin-1 via a binding site that is distinct from a β-glucan binding site of said Dectin-1.

In one embodiment, said binding has a tolerogenic effect on said target cell by mediating NOX-2 dependent ROS production.

In a further aspect, the present invention relates to a composition comprising an annexin-coated particle as defined above.

In one embodiment, said composition further comprises a pharmaceutically acceptable carrier and/or excipient.

In a further aspect, the present invention relates to a product for use in a method of preventing or treating a disease selected from a chronic inflammatory disease, an autoimmune disease, an allergy, and a cancer, said product comprising an annexin-coated particle as defined above, and/or a composition as defined above.

In one embodiment, said annexin of said annexin-coated particle is a pharmaceutically active agent.

In a further aspect, the present invention relates to a method of preparing an annexin-coated particle, preferably as defined above, wherein said method comprises coating a particle comprising a negatively charged phospholipid with an annexin.

In one embodiment, said annexin is any member of the group of annexins, preferably any of annexin A1, annexin A5, and annexin A13, more preferably annexin A1 or annexin A5, and/or is a receptor-binding annexin core domain or a fragment thereof, preferably any of an annexin A1, A5, and A13 core domain or a fragment thereof, more preferably a human annexin A1 or A5 core domain or a fragment thereof.

In one embodiment, said negatively charged phospholipid is any of phosphatidylserine, phosphatidylglycerol, phosphatidic acid, phosphatidylinositol, phosphatidylinositol phosphate, phosphatidylinositol biphosphate, phosphatidylinositol triphosphate, 1,2-dimyristoyl-sn-glycero-3-phosphoglycerol sodium salt (DMPG), 1,2-dimyristoyl-sn-glycero-3-phospho-L-serine sodium salt (DMPS), and 1,2-dimyristoyl-sn-glycero-3-phosphate monosodium salt.

In one embodiment, said particle further comprises any phospholipid selected from phosphatidylcholine, phosphatidylethanolamine, sphingomyelin, and combinations thereof.

In one embodiment, said particle comprises phosphatidylserine, phosphatidylcholine, and phosphatidylethanolamine, preferably comprises phosphatidylserine in a range of from 0.5% to 100%, phosphatidylcholine in a range of from 0% to 99.5%, and phosphatidylethanolamine in a range of from 0% to 20%, wherein said percentages are molar percentages with regard to the total phospholipid content, wherein the sum of the molar percentages of phosphatidylserine, phosphatidylcholine, and phosphatidylethanolamine does not exceed 100%.

In one embodiment, said particle incorporates said negatively charged phospholipid in a particle main body and/or is covered with said negatively charged phospholipid.

In one embodiment, said particle further comprises cholesterol, PEG, a therapeutic agent other than annexin, and/or an antigen.

In one embodiment, said particle is a nano- or microparticle, preferably having a mean diameter in a range of from 20 nm to 1000 nm, preferably ≤400 nm.

In one embodiment, said particle is selected from a lipid vesicle, a micelle, a solid-lipid particle, a polymeric particle, a polysaccharide particle such as an agarose bead, an iron oxide particle, a dendrimer, a viral-based particle, a DNA-based particle, a modified cell, an artificial cell, and a carbon nanotube, wherein said particle is preferably a lipid vesicle and more preferably a unilamellar or multilamellar lipid vesicle.

In one embodiment, said method comprises the following steps:
 a) Providing a phospholipid preparation comprising at least said negatively charged phospholipid, and drying said phospholipid preparation,
 b) Dissolving the dried phospholipid preparation obtained in step a) in an aqueous solution,
 c) Optionally, subjecting the solution comprising phospholipids obtained in step b) to at least one freeze/thaw-cycle,
 d) Extruding the solution comprising phospholipids obtained in step b), or optionally obtained in step c), using an extruder, and thereby obtaining a particle,
 e) Supplementing the particle obtained in step d) with an annexin, and optionally calcium, allowing said annexin to non-covalently couple to said particle, and thereby obtaining an annexin-coated particle,
 wherein said method optionally comprises a step of adding an antigen and/or a therapeutic agent.

For example, in some embodiments, the antigen and/or a therapeutic agent may be added during the process of encapsulation into the medium of the particles, so that the antigen and/or a therapeutic agent gets encapsulated during the formation of the particle. Alternatively, the antigen and/or a therapeutic agent may be added later.

In one embodiment, said extruder is assembled with a 400 nm pore-size membrane.

In one embodiment, said calcium is supplemented at a concentration of from 1 nM to 1000 mM, more preferably in a range of from 0.9 mM to 1 mM.

In a further aspect, the present invention relates to a method of preventing or treating a disease selected from a chronic inflammatory disease, an autoimmune disease, an allergy, and a cancer in a patient, comprising administering to said patient an effective amount of an annexin-coated particle as defined above, a composition as defined above, and/or a product as defined above.

In a further aspect, the present invention relates to the use of an annexin-coated particle for the manufacture of a medicament for a method of preventing or treating a disease selected from a chronic inflammatory disease, an autoimmune disease, an allergy, and a cancer, said annexin-coated particle preferably being as defined above.

DETAILED DESCRIPTION

The present inventors provide a means for effectively blocking off-target binding of annexin preparations (FIG. 1).

This means comprises pre-adsorbing annexin preparations to particles comprising negatively charged phospholipids such as phosphatidylserine, for example lipid vesicles. As disclosed in the present invention, in contrast to soluble annexin, vesicle-bound annexin preparations retain the ability to bind and activate specific annexin-receptor(s), but show no major interaction with cellular surfaces lacking the specific receptor (annexin-receptor-positive and KO cells in FIG. 1 and FIG. 2).

The great advantage of an annexin-coated particle of the present invention is that pre-adsorption to particles comprising negatively-charged phospholipids increases the effective concentration of therapeutic annexin preparations and allows for reduced dosage, which in turn reduces side effects. As annexin-based therapies are currently being developed for medical use by several companies, a commercial demand exists to administer such therapies more effectively by preventing off-target binding.

To prevent the background binding of annexins to negatively charged phospholipids on membranes, particles comprising a negatively charged phospholipid were prepared and loaded with annexin. The binding interface of annexins to target receptors was still available for interaction while the lipid-binding sites were occupied. Accordingly, an annexin-coated particle of the present invention reduces off-target binding to cell membranes, due to the lipid-binding site being occupied, and allows for selective binding to receptors on target cells.

Furthermore, the present inventors demonstrate that the conserved annexin core domain interacts with a target receptor, namely Dectin-1, on a distinct binding site. This interaction induces both phosphorylation of SYK and the production of ROS via activation of NOX-2. Surprisingly, in contrast to β-glucans, the annexin core domain does not induce activation of NfkB nor secretion of pro-inflammatory molecules. Thus, the annexin core domain engages selectively an anti-inflammatory branch of the Dectin-1 signaling pathway and not the classical pro-inflammatory signaling observed upon β-glucan stimulation [10].

The present inventors disclose a receptor-ligand interaction contributing to an essential mechanism of peripheral immune tolerance by priming a tolerogenic phenotype, such as a tolerogenic DC phenotype. Furthermore, activation of NOX-2 by the annexin core domain highlights the importance of NOX-2-dependent ROS production to avoid autoinflammatory processes during physiological tissue turnover and homeostasis.

The herein disclosed molecular pathway of annexin stimulating Dectin-1 and inducing cellular inhibition of DCs via NOX-2-derived ROS represents a novel target for modulating peripheral immune tolerance. Therapeutic manipulation of the annexin/Dectin-1/NOX-2 signalling axis using an annexin-coated particle of the present invention is thus useful in the treatment of autoimmune diseases and for control of immune-evasive tumors. Side effects by off-binding of annexin to negatively charged phospholipids can be prevented by using an annexin-coated particle instead of soluble annexin. The present invention provides a means to enable annexin-mediated therapeutic effects and to prevent off-target binding of annexin by pre-adsorbing the phospholipid-binding sites of annexin using phospholipids.

The term "particle", as used herein, relates to a structure which comprises a negatively charged phospholipid, either by incorporating said phospholipid in its particle main body or by having a coating which comprises said phospholipid. Said particles comprising negatively charged phospholipids are capable of interacting with an annexin or fragment thereof. In one embodiment, a lipid binding site of annexin is bound by a negatively charged phospholipid comprised in said particle. In one embodiment, said lipid binding site of annexin is pre-adsorbed by said binding to said particle comprising a negatively charged phospholipid, and said pre-adsorbing reduces off-target binding of annexin. In one embodiment, said pre-adsorbing reduces off-target binding of annexin to cell membranes, and a receptor-binding site of said annexin is still available for binding to a receptor on a target cell. In one embodiment, a particle is any of a lipid vesicle, a micelle, a solid-lipid particle, a polymeric particle, a polysaccharide particle such as an agarose bead, an iron oxide particle, a dendrimer, a viral-based particle, a DNA-based particle, a modified cell, an artificial cell, and a carbon nanotube, wherein said particle is preferably a lipid vesicle and more preferably a unilamellar or multilamellar lipid vesicle. In one embodiment, a particle such as a lipid vesicle, a micelle, a solid-lipid particle, an agarose bead, a modified cell, and artificial cell may incorporate said negatively charged phospholipid into their particle main body. In one embodiment, a particle such as a polymeric particle, an iron oxide particle, a viral-based particle, or a carbon nanotube may be covered by negatively charged phospholipids. In one embodiment, a particle incorporates said phospholipid in its particle main body and/or is covered by said phospholipid. In one embodiment, a particle is a spherical particle. In one embodiment, a particle comprising annexin has a tolerogenic effect on target cells, preferably by binding to a receptor on said target cell, preferably to any of Dectin-1, DC-SIGN, Lrp1, Complement receptor 3 (ITGAM, CD11b), a formyl peptide receptor (FPR), and a lipoxin receptor. In one embodiment, a particle comprising annexin has a tolerogenic effect on a target cell by binding to Dectin-1 on the surface of said target cell via a binding site of Dectin-1 that is distinct from a β-glucan binding site of said Dectin-1. In one embodiment, said binding of annexin to Dectin-1 has a tolerogenic effect on said target cell by inducing ROS via activation of NOX-2.

The term "particle main body", as used herein, relates to the main supporting structure of a particle. For example, a particle main body may relate to a lipid bilayer of a liposome, to a lipid layer of a micelle, or to a core structure of a polymer, solid-lipid particle, iron particle, and/or nanotube.

The term "vesicle" or "lipid vesicle", as used herein, relates to a structure consisting of liquid enclosed by a lipid bilayer. Vesicles form naturally during the processes of secretion (exocytosis), uptake (endocytosis), and transport of materials within the plasma membrane. Alternatively, they may be prepared artificially, in which case they may also be referred to as liposomes. Liposomes can be used as a vehicle for administration of nutrients and pharmaceutical drugs. Liposomes can be prepared by disrupting biological membranes (such as by sonication). Liposomes are typically composed of phospholipids, such as phosphatidylserine, phosphatidylcholine, and phosphatidylethanolamine. A liposome design may employ surface ligands for targeting certain target tissues. There are several types of liposomes such as the multilamellar vesicle (MLV, with several lipid bilayers), the small unilamellar liposome vesicle (SUV, with one lipid bilayer), the large unilamellar vesicle (LUV), and the cochleate vesicle, and multivesicular liposomes in which one vesicle contains one or more smaller vesicles. In many embodiments, the terms "lipid vesicle" and "liposome" are used interchangeably. In one embodiment, a lipid vesicle relates to a unilamellar or multilamellar lipid vesicle.

The term "annexin", as used herein, relates to a family of calcium- and phospholipid-binding proteins. Over 20 members of the annexin family have been found in all eukaryotic kingdoms as well as plants and animals with the exception of fungi. Annexins have molecular weights ranging between 30 and 40 kDa (only annexin VI is 66 kDa) and possess striking structural features. Annexins' aminoterminal domains are diverse in sequence and length (ranging from 11 to 196) on each annexin member. In contrast the carboxy-terminal regions consisting of four (eight only for annexin VI) a-helical domains composed of about 70 amino acid residues are well conserved among annexins. The calcium- and phospholipid-binding sites are located in the carboxy-terminal domains. The $Ca^{2+}$ binding similarities of all the annexins is due to their common primary structure, a unique N-terminal domain (the "tail") and the conserved C-terminal domain (the "core"). With the exception of annexin VI, the conserved C-terminal domain is always composed of 4 repeats (annexin VI having 8) of ~70 amino acids containing an increased homology region called the "endonexin fold". In addition to the C terminal core the annexins contain a significantly more variable N terminal head. It is this domain which endows each annexin with unique functions in a diverse range of cellular processes including; endo- and exocytosis, cytoskeletal regulation and membrane conductance and organisation. Annexin lipid binding is mediated by a C-terminal core domain highly conserved among all annexin family members. The term "member of the group of annexins", as used herein, relates to any member of the annexin family including annexins from any species. Calcium ions typically bind on the convex side of an annexin molecule, particularly to carbonyl oxygens in the loop connecting the A and B helices of annexin and to a bidentate carboxyl group from a glutamic acid residue or an aspartic acid residue located in the loop connecting helices D and E. When calcium is bound to annexin, hydrophobic lateral chains are exposed in the otherwise mainly hydrophilic convex surface. These hydrophobic residues are commonly assumed to contribute to the interaction with bilayers by establishing van der Waals forces with the hydrophobic acyl chains of phospholipids. In one embodiment, a method of preparing an annexin-coated particle preferably comprises using calcium to enhance the interaction of annexin with phospholipids. In one embodiment, a method of preparing an annexin-coated particle comprises supplementing a particle with annexin and preferably calcium, said calcium preferably at a concentration in a range of from 1 nM to 1000 mM, more preferably in a range of from 0.9 mM to 1 mM.

Furthermore, the term "annexin" in context of the invention in some preferred embodiments shall comprise proteins having an amino acid sequence with at least 80%, preferably 85%, 90%, 95%, 96%, 97%, 98% or 99% sequence identity to an amino acid sequence of an, preferably human, annexin A1, annexin A5, and/or annexin A13. The amino acid sequence of the annexins can be derived from the UniProt database in the version of February 2019 with the following database entries: Po4083 (human annexin A1), Po8758 (human annexin A5), and P27216 (annexin A13) (uniprot.org/; see also Nucleic Acids Research, Volume 45, Issue D1, 4 Jan. 2017, Pages D158-D169).

In the context of the present invention, the terms "annexin core domain" and "receptor-binding annexin core domain" shall be understood as indicating/representing the minimal fragment of the polypeptide for annexin (or homologs thereof), which is necessary and sufficient to bind to a receptor such as C-type lectin receptor and/or LRP-1, or functional fragments thereof. This ability (biological function) may be tested in a number of art known methods. Also, the term shall particularly comprise the vertebrate, in particular mammalian (in particular human) annexin gene and/or protein and/or mRNA and/or the fragment (core domain) as described herein. The term also covers the annexin core domain in different preparations, such as in the cellular context, a cell recombinantly expressing said core domain, purified from the cell, and fractions, in particular biologically active fractions, thereof. The annexin core domain that can be used in the method according to the present invention can be derived from any of the known annexins or functional fragments (i.e. able to bind to the receptors as described herein) thereof, and is preferably selected from the group of the human or murine annexin 1, 5, and 13 core domain. In one embodiment, said annexin core domain preferably relates to any of SEQ ID Nos. 1 to 3 and 6 to 8 of WO 2017/211964 A1 which are herein incorporated by reference.

In one embodiment, a "target receptor" targeted by annexin may relate to a receptor selected from Dectin-1, DC-SIGN and murine homologs thereof, Lrp1, Complement receptor 3 (ITGAM, CD11b), receptors of the formyl peptide receptor (FPR) family such as FPR1, FPR2, and FPR3, and lipoxin receptors, as well as homologs thereof from other species. In one embodiment, the terms "target receptor" and "annexin receptor" are used interchangeably. In one embodiment, a receptor bound by annexin may also relate to a previously unknown receptor which is specifically bound by annexin. In one embodiment, said receptor-binding annexin core domain binds to a receptor selected from Dectin-1, DC-SIGN and murine homologs thereof, Lrp1, Complement receptor 3 (ITGAM, CD11b), receptors of the formyl peptide receptor (FPR) family such as FPR1, FPR2, and FPR3, and lipoxin receptors.

The term "fragment thereof", as used herein, relates to a minimal fragment of the polypeptide for annexin (or homologs thereof), which is necessary and sufficient to bind to a receptor on a target cell, such as Dectin-1. In an alternative embodiment, the term "fragment thereof" relates to a minimal fragment of a receptor, which is necessary and sufficient to bind to a core domain of annexin.

In the context of the present invention, the terms "C-type lectin receptor", "Dectin-1", "DC-SIGN", "LRP-1", "FPR" shall be understood as indicating/representing the minimal fragment of the receptor(s), which is necessary and sufficient to bind to an annexin core domain. This ability may further be tested in a number of art known methods as described in the respective literature. Also, the term shall comprise the mammalian (in particular mouse) homolog of the human receptor gene and/or protein and/or mRNA and/or the fragment (binding part, fragment or domain) as described herein. The term also covers the receptor(s) and/or the minimal fragment of the receptor(s) in different preparations, such as in the cellular context, a cell (recombinantly) expressing said receptor(s) and/or the minimal fragment of the receptor(s), purified from the cell, and fractions thereof.

The present inventors herein disclose a tolerogenic role for the pattern-recognition receptor Dectin-1 upon binding to annexin, such as externalized annexins on cells such as apoptotic cells. Apoptotic cells induce a tolerogenic phenotype in dendritic cells (DCs) leading to peripheral tolerance, e.g. against apoptotic cell-derived self-antigens. During apoptosis, the cell surface becomes rapidly rearranged by exposure of negatively charged phospholipids as well as by externalization of cytosolic annexins serving as immune-suppressive signals towards phagocytosing DCs. As disclosed herein, Dectin-1 recognizes annexin via a binding site which is distinct from the β-glucan binding site of said Dectin-1. Accordingly, annexin, such as phospholipid-bound annexin, binds to a distinct binding site of Dectin-1 not interfering with the binding of pathogen-derived β-glucans. Thereby, the annexin core domain induces phosphorylation of the spleen tyrosine kinase (SYK) in turn activating NADPH oxidase-2 (NOX-2). In contrast to pathogen-derived β-glucans, annexin-induced Dectin-1 signaling is characterized by NOX-2-dependent production of moderate ROS-levels and does not activate NF-κB. In one embodiment, binding of an annexin-coated particle via annexin to a receptor such as Dectin-1 on a target cell induces a tolerogenic phenotype in said target cell, i.e. said binding has a tolerogenic effect on said target cell. In one embodiment, said binding results in the development of peripheral tolerance.

The term "target cell", as used herein, relates to cells that have the ability to bind to an annexin, for example cells having a receptor that is capable of binding to an annexin. In one embodiment, said receptor is any of Dectin-1, DC-SIGN and murine homologs thereof, Lrp1, Complement receptor 3 (ITGAM, CD11b), receptors of the formyl peptide receptor (FPR) family such as FPR1, FPR2, and FPR3, and lipoxin receptors. A target cell of the invention may be selected from any type of mammalian, in particular human, cells. In one embodiment, target cells relate to cells selected from any of dendritic cells, macrophages, monocytes, microglia, endothelial cells, epithelial cells, neutrophils, and any other cells expressing a target receptor. In one embodiment, a target cell may relate to a cancer cell.

The term "phospholipid", as used herein, relates to a class of lipids that are a major component of all cell membranes. Phospholipids can form lipid bilayers because of their amphiphilic characteristics. The structure of the phospholipid molecule typically comprises two hydrophobic fatty acid "tails" and a hydrophilic "head" consisting of a phosphate group. The two components are typically joined together by a glycerol molecule. The phosphate groups can be modified with simple organic molecules such as choline, ethanolamine or serine. When placed in aqueous solutions, phospholipids are driven by hydrophobic interactions that result in the fatty acid tails aggregating to minimize interactions with water molecules. There are diacylglycyl-based phospholipids such as phosphatidic acid, phosphatidylethanolamine, phosphatidylcholine, phosphatidylserine, phosphatidylinositol, phosphatidylinositol phosphate, phosphatidylinositol bisphosphate, phosphatidylinositol triphosphate, and phosphosphingolipids. In one embodiment, a phospholipid may also relate to a phospholipid derivative, such as synthetic phospholipid derivatives, including derivatives of phosphatidic acid (DPMA, DPPA, DSPA), phosphatidylcholine (DDPC, DLPC, DMPC, DPPC, DSPC, DOPC, POPC, DEPC), phosphatidylglycerol (DMPG, DPPG, DSPG, POPG), phosphatidylethanolamine (DMPE, DPPE, DSPE DOPE), and phosphatidylserine (DOPS).

The term "negatively charged phospholipid", as used herein, relates to phospholipids, which have a negative net charge at physiological pH. In contrast thereto, there are also neutral phospholipids in which the phospholipid head group comprises a negative charge of phosphate and a positive charge of, e.g., an amine group, thus resulting in a net neutral charge at physiological pH. Negatively charged phospholipids may include, but are not limited to phosphatidylserine, phosphatidylglycerol, phosphatidic acid, phosphatidylinositol, phosphatidylinositol phosphate, phosphatidylinositol biphosphate, phosphatidylinositol triphosphate, 1,2-dimyristoyl-sn-glycero-3-phosphoglycerol sodium salt (DMPG), 1,2-dimyristoyl-sn-glycero-3-phospho-L-serine sodium salt (DMPS), and 1,2-dimyristoyl-sn-glycero-3-phosphate monosodium salt. In one embodiment, structural elements of a negatively charged phospholipid allow for optimal interaction with annexin, such as an oxygen-atom in a carboxyl group and an alpha-amino group stabilizing an H-bridge.

The term "incorporates", as used herein, relates to a feature of a particle, wherein said particle comprises a component, such as a phospholipid, in its main body. Said incorporating may relate to, for example, comprising said phospholipid as part of a lipid-solid composite material. In one embodiment, said incorporating relates to comprising said phospholipid in a lipid layer, preferably a lipid bilayer of a liposome. In one embodiment, a particle may both incorporate a phospholipid and be covered with a phospholipid.

The term "covered", as used herein, relates to a feature of a particle, wherein said particle comprises a component such as a phospholipid on its surface. In one embodiment, said phospholipid is part of the particle's surface, for example the surface of a liposome, and/or coats the particle's surface, for example a lipid layer covering an iron oxide particle.

The term "nano- or microparticle", as used herein, relates to particles between 1 and 100 nm in size, or particles between 0.1 and 100 μm in size, respectively. Nano- or microparticles may be produced from a wide variety of materials, such as ceramics, glass, polymers, biomolecules, and metals.

The term "artificial cell", as used herein, relates to an engineered particle that mimics one or many functions of a biological cell. The term does not refer to a specific physical entity, but rather to the idea that certain functions or structures of biological cells can be replaced or supplemented with a synthetic entity. Typically, artificial cells are biological or polymeric membranes which enclose biologically active materials. As such, nanoparticles, liposomes, polymerosomes, microcapsules and a number of other particles may be used to prepare artificial cells. Membranes for artificial cells can be made of simple polymers, crosslinked proteins, lipid membranes or polymer-lipid complexes. Further, membranes can be engineered to comprise negatively charged phospholipids and/or annexin.

The term "modified cell", as used herein, relates to a cell which has been modified, e.g. by genetically modifying said cell, to comprise/produce a negatively charged phospholipid and/or an annexin. In one embodiment, an unmodified comprises/produces a negatively charged phospholipid and/or annexin, and modification of said cell results in increased levels of said negatively charged phospholipid and/or said annexin in said modified cell compared to said unmodified cell.

The term "diameter", as used herein, relates to any straight line segment that passes through the center of a spherical particle and whose endpoints lie on the spherical particle. In cases of non-spherical particles, a diameter relates to the longest line segment that passes through the center of said non-spherical particle and whose endpoints lie on the particle. In one embodiment, a mean diameter relates to the mean of the diameters of particles comprised in a batch of particles.

The term "composition", as used herein, relates to a composition comprising at least an annexin-coated particle of the invention. The annexin-coated particles of the invention can be admixed with suitable auxiliary substances and/or additives to obtain a pharmaceutically acceptable composition and/or a product of the present invention. Such substances comprise pharmacological acceptable substances, which increase the stability, solubility, biocompatibility, or biological half-life of the interacting annexin-coated particles or comprise substances or materials, which have to be included for certain routs of application like, for example, intravenous solution, sprays, band-aids or pills. Carriers, excipients and strategies to formulate a pharmaceutical composition and/or a pharmaceutical product, for example to be administered systemically or topically, by any conventional route, in particular enterally, e.g. orally, e.g. in the form of tablets or capsules, parenterally, e.g. in the form of injectable solutions or suspensions, topically, e.g. in the form of lotions, gels, ointments or creams, or in nasal or a suppository form are well known to the person of skill and described in the respective literature.

In one embodiment, a composition of the present invention further comprises one or more immune stimulatory compounds such as adjuvants. An "adjuvant" is an agent that enhances the production of an immune response in a non-specific manner. Common adjuvants include suspensions of minerals (alum, aluminum hydroxide, aluminum phosphate) onto which the fusion protein of the invention is adsorbed; emulsions, including water-in-oil, and oil-in-water (and variants thereof, including double emulsions and reversible emulsions), liposaccharides, lipopolysaccharides, immunostimulatory nucleic acids (such as CpG oligonucleotides), liposomes, Toll-like Receptor agonists (particularly, TLR2, TLR4, TLR7/8 and TLR9 agonists), and various combinations of such components.

In one embodiment, a composition and/or an annexin-coated particle of the present invention further comprises a therapeutic agent other than annexin and/or an antigen. Said therapeutic agent other than annexin and/or an antigen may be encapsulated by said particle and/or may be coupled to the surface of the particle. In one embodiment, said therapeutic agent other than annexin is a chemotherapeutic substance. In one embodiment, said annexin-coated particle encapsulating a therapeutic agent other than annexin is for use in drug delivery. In one embodiment, an annexin-coated particle, preferably further comprising an antigen, is for use in a tumor vaccination. In one embodiment, said antigen is an autoantigen, an allergen, and/or a cancer antigen. In one embodiment, an annexin-coated particle, optionally further comprising a therapeutic agent, is used for targeting a target cell, such as a cell expressing any of Dectin-1, DC-SIGN and murine homologs thereof, Lrp1, Complement receptor 3 (ITGAM, CD11b), receptors of the formyl peptide receptor (FPR) family such as FPR1, FPR2, and FPR3, and lipoxin receptors. In one embodiment, a method of preparing a particle of the present invention comprises a step of adding an antigen and/or a therapeutic agent. Techniques for adding an antigen and/or a therapeutic agent to a particle, e.g. by incorporation into said particle and/or by coupling to the surface of said particle, are known to a person skilled in the art. In one embodiment, adding an antigen and/or a therapeutic agent to a particle may relate to an addition before, during, or after the preparation of said particle.

The term "product", as used herein, relates to any of the inventive particles, compounds and compositions, and in particular relates to a pharmaceutical acceptable formulation of an annexin-coated particle of the present invention. In one embodiment, a product of the present invention further comprises additional pharmaceutically active ingredients for treating or preventing autoimmune diseases, chronic inflammatory diseases, allergies or cancer, i.e. chemotherapeutics. In one embodiment, the terms "composition" and "product" are used interchangeably. In many of the embodiments, said product is for use in medicine. In one embodiment, said product is a medicament. A product of the present invention is particularly useful in the prevention and treatment of autoimmune diseases, chronic inflammatory diseases, allergies, and cancer. In one embodiment, a product of the present invention is for use in a cancer vaccination.

The term "pharmaceutically active agent", as used herein, relates to an agent which evokes a therapeutic effect. In one embodiment, annexin binds to a receptor on a target cell and evokes a tolerogenic effect on said target cell.

The term "non-covalently coupled", as used herein, relates to a binding of annexin to a particle which is not mediated by a covalent bond between annexin and a component of said particle. A non-covalent coupling may be a related to an electrostatic interaction, a n-effect, van der Waals forces, and/or hydrophobic effects. In one embodiment, the term "non-covalently coupled" does not relate to coupling mediated via a FLAG-tag. In one embodiment, annexin or a fragment thereof couples to said particle via an interaction of a lipid-binding domain of annexin to a negatively charged phospholipid comprised in said particle. In one embodiment, coupling of said annexin to a particle comprising a negatively charged phospholipid results in the occupation of annexin's lipid binding domain, so that said occupied lipid binding domain is not available for off-target binding to cell membranes. In one embodiment, said annexin with occupied lipid binding domain binds specifically to a receptor on a target cell via a receptor binding domain of annexin. In one embodiment, the non-covalent coupling requires calcium ions. In many of the embodiments, annexin is coupled to the surface of a particle. In one embodiment, annexin is coupled to a phospholipid comprised within the interior space of a particle and/or is coupled to a phospholipid on the surface of a particle. In one embodiment, an annexin is not covalently coupled to a linker molecule, such as PEG, which is non-covalently coupled to said particle.

The present inventors disclose that annexin coupled to a particle binds to receptors on target cells and does not exhibit off-target binding to cells which do not comprise an annexin-receptor. In contrast thereto, soluble annexin, which is not bound to a particle, exhibits off-target binding to cells not expressing an annexin receptor. In one embodiment, said reduction of off-target binding by pre-adsorbing annexin to a particle is demonstrated in FIG. 3*b* and Tables 1-3. In one embodiment, preoccupation of the annexin lipid-binding site by non-covalently coupling annexin to a particle reduces annexin side effects caused by off-target binding.

The term "supplementing", as used herein, relates to mixing and/or incubating a particle, a preparation comprising vesicles and/or a phospholipid preparation for preparing vesicles with other components, such as annexin, an annexin core domain, calcium, and/or an antigen. In one embodiment, supplementing relates to incubating a vesicle preparation with annexin, and optionally calcium, for 1-48 h at a temperature of from 1° C. to 25° C., preferably over night at a temperature of from 4° C. to 8° C. In one embodiment, a preparation comprising vesicles and/or a phospholipid preparation for preparing vesicles is preferably supplemented with calcium. In one embodiment, said incubating further comprises agitating said supplemented vesicle preparation and/or phospholipid preparation using a shaker, roller, or an other means for agitation. In one embodiment, said supplementing comprises supplementing with calcium at a concentration of at least 0.001 mM, preferably at a concentration of 0.9-1 mM. In one embodiment, supplementing comprises supplementing with an annexin, a receptor-binding annexin core domain, and/or a fragment thereof, in molar excess over the negatively charged phospholipids of a phospholipid preparation and/or of a vesicle preparation. In one embodiment, supplementing comprises supplementing with an annexin, a receptor-binding annexin core domain, and/or a fragment thereof, and calcium. Supplementing may further comprise supplementing with an antigen and/or a therapeutic agent, wherein said antigen and/or therapeutic agent may be encapsulated by said particle, or may be coupled to said particle, e.g. as an annexin fusion protein, as a lipid-anchored protein, or via a PEGylation.

The term "administering", as used herein, relates to the administration of an agent, e.g. an annexin-coated particle, a composition, and/or a product of the present invention, which can be accomplished by any method which allows the agent to reach the target cells. These methods include, e.g., injection, deposition, implantation, suppositories, oral ingestion, inhalation, topical administration, or any other method of administration where access to the target cells by the agent is obtained. Injections can be, e.g., intravenous, intradermal, subcutaneous, intramuscular or intraperitoneal. Implantation includes inserting implantable drug delivery systems, e.g., microspheres, coated microparticles, hydrogels, polymeric reservoirs, cholesterol matrices, polymeric systems, e.g., matrix erosion and/or diffusion systems and non-polymeric systems, e.g., compressed, fused or partially fused pellets. Suppositories include glycerin suppositories. Oral ingestion doses can be enterically coated. Inhalation includes administering the agent with an aerosol in an inhalator, either alone or attached to a carrier that can be absorbed. The agent can be suspended in liquid, e.g., in dissolved or colloidal form. The liquid can be a solvent, partial solvent or non-solvent. In many cases, water or an organic liquid can be used.

An "effective amount" is an amount of the annexin-coated particle, the pharmaceutical composition, or the product as described herein that alleviates symptoms as found for the disease and/or condition.

The term "patient", as used herein, relates to a human or an animal, preferably a mammal. Treating of a patient is meant to include, e.g., preventing, treating, reducing the symptoms of, or curing the disease or condition, i.e. immunological diseases such as immunodeficiency, infectious diseases or cancer. The invention also includes an annexin-coated particle for use in a method of treating a subject at risk for infectious diseases or cancer, wherein a therapeutically effective amount of annexin-coated particle is provided. Being at risk for the disease can result from, e.g., a family history of the disease, a genotype which predisposes to the disease, or phenotypic symptoms which predispose to the disease.

The term "cancer", as used herein, preferably relates to a solid tumor, such as, for example, selected from breast, bone, ovarian, liver, kidney, and lung cancer.

In some further specifically preferred embodiments the present invention relates to the subject matter of the following items:

Item 1: An annexin-coated particle, comprising a negatively charged phospholipid and an annexin non-covalently coupled thereto.

Item 2: The annexin-coated particle according to item 1, wherein said annexin is any member of the group of annexins, preferably any of annexin A1, annexin A5, and annexin A13, more preferably annexin A1 or annexin A5, and/or is a receptor-binding annexin core domain or a fragment thereof, preferably any of an annexin A1, A5, and A13 core domain or a fragment thereof, more preferably a human annexin A1 or A5 core domain or a fragment thereof.

Item 3: The annexin-coated particle according to item 1 or 2, wherein said negatively charged phospholipid is any of phosphatidylserine, phosphatidylglycerol, phosphatidic acid, phosphatidylinositol, phosphatidylinositol phosphate, phosphatidylinositol biphosphate, phosphatidylinositol triphosphate, 1,2-dimyristoyl-sn-glycero-3-phosphoglycerol sodium salt (DMPG), 1,2-dimyristoyl-sn-glycero-3-phospho-L-serine sodium salt (DMPS), and 1,2-dimyristoyl-sn-glycero-3-phosphate monosodium salt.

Item 4: The annexin-coated particle according to any one of the foregoing items, wherein said particle further comprises any phospholipid selected from phosphatidylcholine, phosphatidylethanolamine, sphingomyelin, and combinations thereof.

Item 5: The annexin-coated particle according to any one of the foregoing items, wherein said particle comprises phosphatidylserine, phosphatidylcholine, and phosphatidylethanolamine.

Item 6: The annexin-coated particle according to item 5, wherein said particle comprises phosphatidylserine in a range of from 0.5% to 100%, phosphatidylcholine in a range of from 0% to 99.5%, and phosphatidylethanolamine in a range of from 0% to 20%, wherein said percentages are molar percentages with regard to the total phospholipid content, wherein the sum of the molar percentages of phosphatidylserine, phosphatidylcholine, and phosphatidylethanolamine does not exceed 100%.

Item 7: The annexin-coated particle according to any one of the foregoing items, wherein said particle incorporates said negatively charged phospholipid in a particle main body and/or is covered with said negatively charged phospholipid.

Item 8: The annexin-coated particle according to any one of the foregoing items, wherein said particle further comprises cholesterol, PEG, a therapeutic agent other than annexin, and/or an antigen.

Item 9: The annexin-coated particle according to any one of the foregoing items, wherein said particle is a nano- or microparticle.

Item to: The annexin-coated particle according to any one of the foregoing items, wherein said particle has a mean diameter in a range of from 20 nm to 1000 nm, preferably 400 nm.

Item 11: The annexin-coated particle according to any one of the foregoing items, wherein said particle is selected from a lipid vesicle, a micelle, a solid-lipid particle, a polymeric particle, a polysaccharide particle such as an agarose bead, an iron oxide particle, a dendrimer, a viral-based particle, a DNA-based particle, a modified cell, an artificial cell, and a carbon nanotube.

Item 12: The annexin-coated particle according to any one of the foregoing items, wherein said particle is a lipid vesicle, preferably a unilamellar or multilamellar lipid vesicle.

Item 13: The annexin-coated particle according to any one of the foregoing items, wherein said particle is capable of binding to a receptor on a target cell, preferably to any of Dectin-1, DC-SIGN, Lrp1, Complement receptor 3 (ITGAM, CD11b), a formyl peptide receptor (FPR), and a lipoxin receptor.

Item 14: The annexin-coated particle according to item 13, wherein said particle is capable of binding to Dectin-1 via a binding site that is distinct from a β-glucan binding site of said Dectin-1.

Item 15: The annexin-coated particle according to item 13 or 14, wherein said binding has a tolerogenic effect on said target cell by mediating NOX-2 dependent ROS production.

Item 16: A composition comprising an annexin-coated particle as defined in any of items 1-15.

Item 17: The composition according to item 16, wherein said composition further comprises a pharmaceutically acceptable carrier and/or excipient.

Item 18: A product for use in a method of preventing or treating a disease selected from a chronic inflammatory disease, an autoimmune disease, an allergy, and a cancer, said product comprising an annexin-coated particle as defined in any of items 1-15, and/or a composition as defined in any of items 16-17.

Item 19: The product for use according to item 18, wherein said annexin of said annexin-coated particle is a pharmaceutically active agent.

Item 20: A method of preparing an annexin-coated particle, preferably as defined in any of items 1-15, wherein said method comprises coating a particle comprising a negatively charged phospholipid with an annexin.

Item 21: The method according to item 20, wherein said annexin is any member of the group of annexins, preferably any of annexin A1, annexin A5, and annexin A13, more preferably annexin A1 or annexin A5, and/or is a receptor-binding annexin core domain or a fragment thereof, preferably any of an annexin A1, A5, and A13 core domain or a fragment thereof, more preferably a human annexin A1 or A5 core domain or a fragment thereof.

Item 22: The method according to any of items 20-21, wherein said negatively charged phospholipid is any of phosphatidylserine, phosphatidylglycerol, phosphatidic acid, phosphatidylinositol, phosphatidylinositol phosphate, phosphatidylinositol biphosphate, phosphatidylinositol triphosphate, 1,2-dimyristoyl-sn-glycero-3-phosphoglycerol sodium salt (DMPG), 1,2-dimyristoyl-sn-glycero-3-phospho-L-serine sodium salt (DMPS), and 1,2-dimyristoyl-sn-glycero-3-phosphate monosodium salt.

Item 23: The method according to any of items 20-22, wherein said particle further comprises any phospholipid selected from phosphatidylcholine, phosphatidylethanolamine, sphingomyelin, and combinations thereof.

Item 24: The method according to any of items 20-23, wherein said particle comprises phosphatidylserine, phosphatidylcholine, and phosphatidylethanolamine, preferably comprises phosphatidylserine in a range of from 0.5% to 100%, phosphatidylcholine in a range of from 0% to 99.5%, and phosphatidylethanolamine in a range of from 0% to 20%, wherein said percentages are molar percentages with regard to the total phospholipid content, wherein the sum of the molar percentages of phosphatidylserine, phosphatidylcholine, and phosphatidylethanolamine does not exceed 100%.

Item 25: The method according to any of items 20-24, wherein said particle incorporates said negatively charged phospholipid in a particle main body and/or is covered with said negatively charged phospholipid.

Item 26: The method according to any of items 20-25, wherein said particle further comprises cholesterol, PEG, a therapeutic agent other than annexin, and/or an antigen.

Item 27: The method according to any of items 20-26, wherein said particle is a nano- or microparticle, preferably having a mean diameter in a range of from 20 nm to 1000 nm, preferably 400 nm.

Item 28: The method according to any of items 20-27, wherein said particle is selected from a lipid vesicle, a micelle, a solid-lipid particle, a polymeric particle, a polysaccharide particle such as an agarose bead, an iron oxide particle, a dendrimer, a viral-based particle, a DNA-based particle, a modified cell, an artificial cell, and a carbon nanotube, wherein said particle is preferably a lipid vesicle and more preferably a unilamellar or multilamellar lipid vesicle.

Item 29: The method according to any of items 20-28, wherein said method comprises the following steps:
a) Providing a phospholipid preparation comprising at least said negatively charged phospholipid, and drying said phospholipid preparation,
b) Dissolving the dried phospholipid preparation obtained in step a) in an aqueous solution,
c) Optionally, subjecting the solution comprising phospholipids obtained in step b) to at least one freeze/thaw-cycle,
d) Extruding the solution comprising phospholipids obtained in step b), or optionally obtained in step c), using an extruder, and thereby obtaining a particle,
e) Supplementing the particle obtained in step d) with an annexin, and optionally calcium, allowing said annexin to non-covalently couple to said particle, and thereby obtaining an annexin-coated particle,
wherein said method optionally comprises a step of adding an antigen and/or a therapeutic agent.

Item 30: The method according to item 29, wherein said extruder is assembled with a 400 nm pore-size membrane.

Item 31: A method of preventing or treating a disease selected from a chronic inflammatory disease, an autoimmune disease, an allergy, and a cancer in a patient, comprising administering to said patient an effective amount of an annexin-coated particle as defined in any of items 1-15, a composition as defined in any of items 16-17, and/or a product as defined in any of items 18-19.

Item 32: Use of an annexin-coated particle for the manufacture of a medicament for a method of preventing or treating a disease selected from a chronic inflammatory disease, an autoimmune disease, an allergy, and a cancer, said annexin-coated particle preferably being as defined in any of items 1-15.

BRIEF DESCRIPTION OF THE FIGURES

The present invention is now further described by reference to the following figures.

All methods mentioned in the figure descriptions below were carried out as described in detail in the examples.

Phagocytosis experiments were analysed after 3 h of incubation on 37° C. or 4° C. as control (a-c) Spleen tyrosine kinase (SYK)-phosphorylation in bone marrow-derived dendritic cells (BMDCs) or MM6 cells was analyzed by flow cytometry. Cells were treated as indicated in the presence of phosphatase inhibitor sodium vanadate (1 mM) (a and b) or without phosphatase inhibition (c) and stained intracellular by an antibody against p-SYK. (d-g) Intracellular ROS levels were determined by $H_2DCFDA$ after 2 h. The cells were treated with indicated ligands for 1.5 h and further incubated with $H_2DCFDA$ for 30 min. Phorbol 12-myristate 13-acetate (PMA) and the Dectin-1 ligand depleted zymosan (DZ) were used as positive controls. Co-treatment of annexin (Anx) A1ΔN with the ROS scavenger 6-Hydroxy-2,5,7,8-tetramethylchroman-2-carbonsäure (Trolox) as well as heat inactivated (h.i.) AnxA1ΔN were used as negative controls. Fluorescein isothiocyanate (FITC), median fluorescence intensity (MFI), phosphatidylserine (PS)-containing vesicles (PSV). Results represent one representative experiment out of two (c, f, g) or means±s.d. of three (mAnxA5, h.i. mAnxA1ΔN, DZ), four (mAnxA1ΔN+Trolox), eight (msAnxA1ΔN [500 nM], PMA) or nine (msAmA1[1000 nM]) independent experiments (d and e). *p<0.001, p<0.01, *p<0.05, n.s.=not significant, n.d.=no FITC-MFI increase detected (unpaired, two-tailed t-test).

Figure 5:
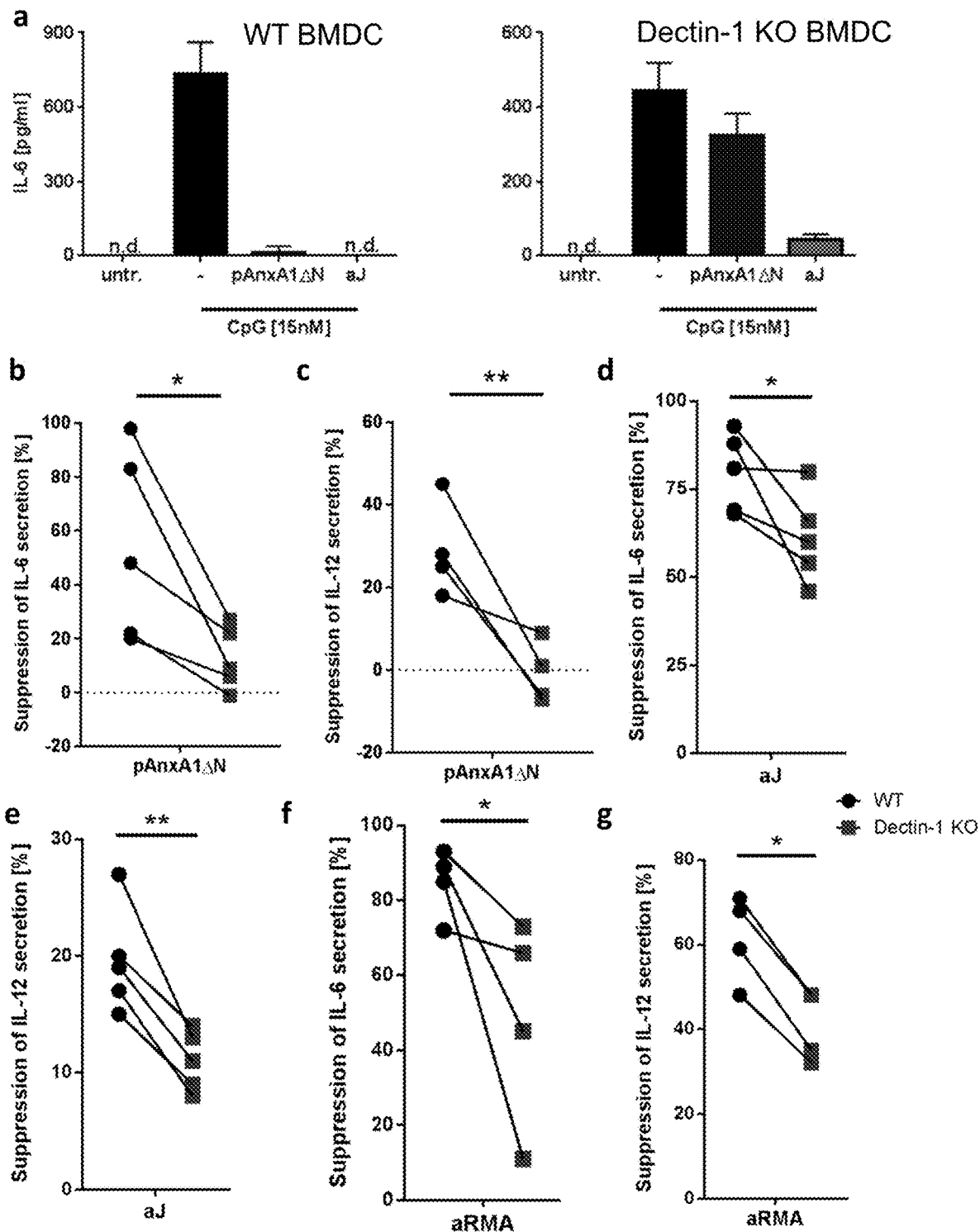

FIG. 5 shows Dectin-1 mediating immunosuppressive effects of apoptotic cells and annexins.

A total of $10^5$ BMDCs were incubated with pAnxA1ΔN (1000 nM), apoptotic Jurkat T-cells (aJ; ratio of 0.5:1 or 0.1:1) or apoptotic RMA cells (aRMA; ratio of 4:1) for 8 h. After pre-incubation, BMDCs were stimulated over night with the TLR agonist CpG (15-40 nM). Cytokine concentrations in the supernatants were analyzed by ELISA 16-24 h after stimulation.
(a) Representative suppression experiment performed with WT (left) and Dectin-1 KO (right) BMDCs. In WT cells pAnxA1ΔN prevented the secretion of IL-6 compared to CpG-treated cells without annexin pre-incubation. In contrast, the suppressive capacity of annexin was reduced in Dectin-1 KO BMDCs.

(b-g) Quantification of three to five independent experiments. The suppression of cytokine secretion is normalized to CpG-stimulation only ((100−treated/CpG only)*100).

(h-i) CD80 surface staining was analyzed 2-3 d after CpG stimulation by flow cytometry. (h) Representative histogram of CD80 expression in WT (left) and Dectin-1 KO BMDCs (right) with indicated treatments. (i) Quantification of CD80 surface marker expression of five independent experiments. The suppression of CD80 expression is normalized to CpG-stimulation only minus untreated (100−((treated−untreated)/(CpG only−untreated))*100). Results represent means out of at least three independent experiments. *$p<0.001$, $p<0.01$, *$p<0.05$ (paired, two-tailed t-test). procaryotically expressed AnxA1 core domain (pAnxA1ΔN), eukaryotically expressed AnxA1 core domain (eAnxA1ΔN).

Figure 6:
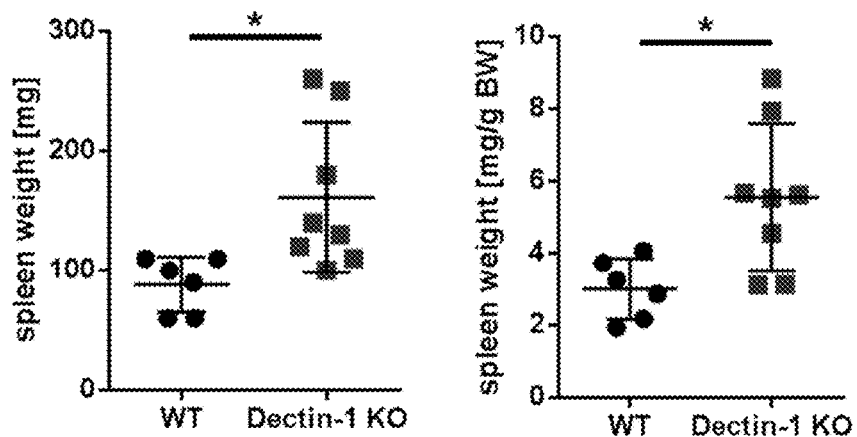
Figure 6:
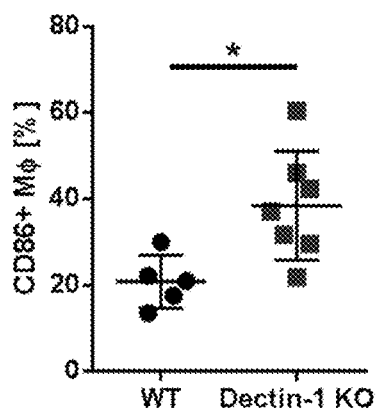
Figure 6:
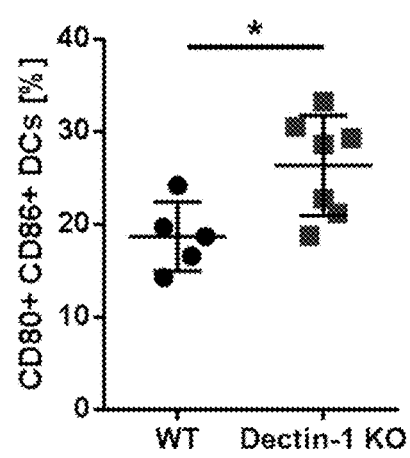
Figure 6:
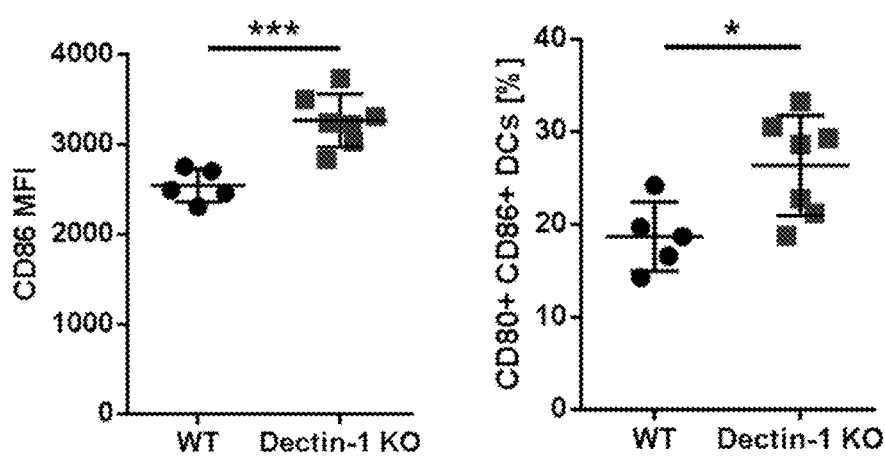
Figure 6:
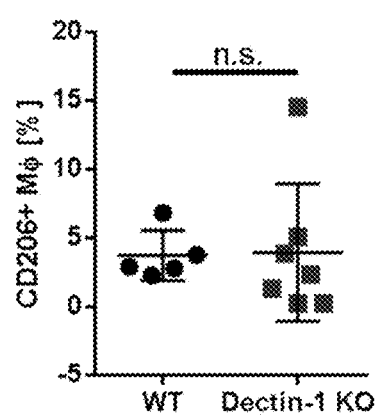

FIG. 6 shows aged Dectin-1 KO mice exhibiting symptoms of autoimmunity.

(a) Spleen weight of aged WT and Dectin-1 KO mice.

(b-f) DCs (CD11c+ and MHCII+) and macrophages (F4/80+ and MHCII+) of isolated splenocytes were stained in combination with activation markers CD80 and CD86 as well as anti-inflammatory M2-macrophage marker CD206 and analyzed by flow cytometry. (g-i) Heparin-treated blood samples from cardiocentesis were centrifuged for 10 min by 18,000×g at 4° C. Supernatants were collected and analyzed for indicated auto-antibodies against dsDNA by ELISA. The dashed line represents the absorbance of the negative control casein only. Results represent the mean±s.d. of 4-8 mice per group. *$p<0.01$ $p<0.01$, *$p<0.05$, n.s.=not significant (unpaired, two-tailed t-test). Body weight (BW), mean fluorescence intensity (MFI).

Figure 7:
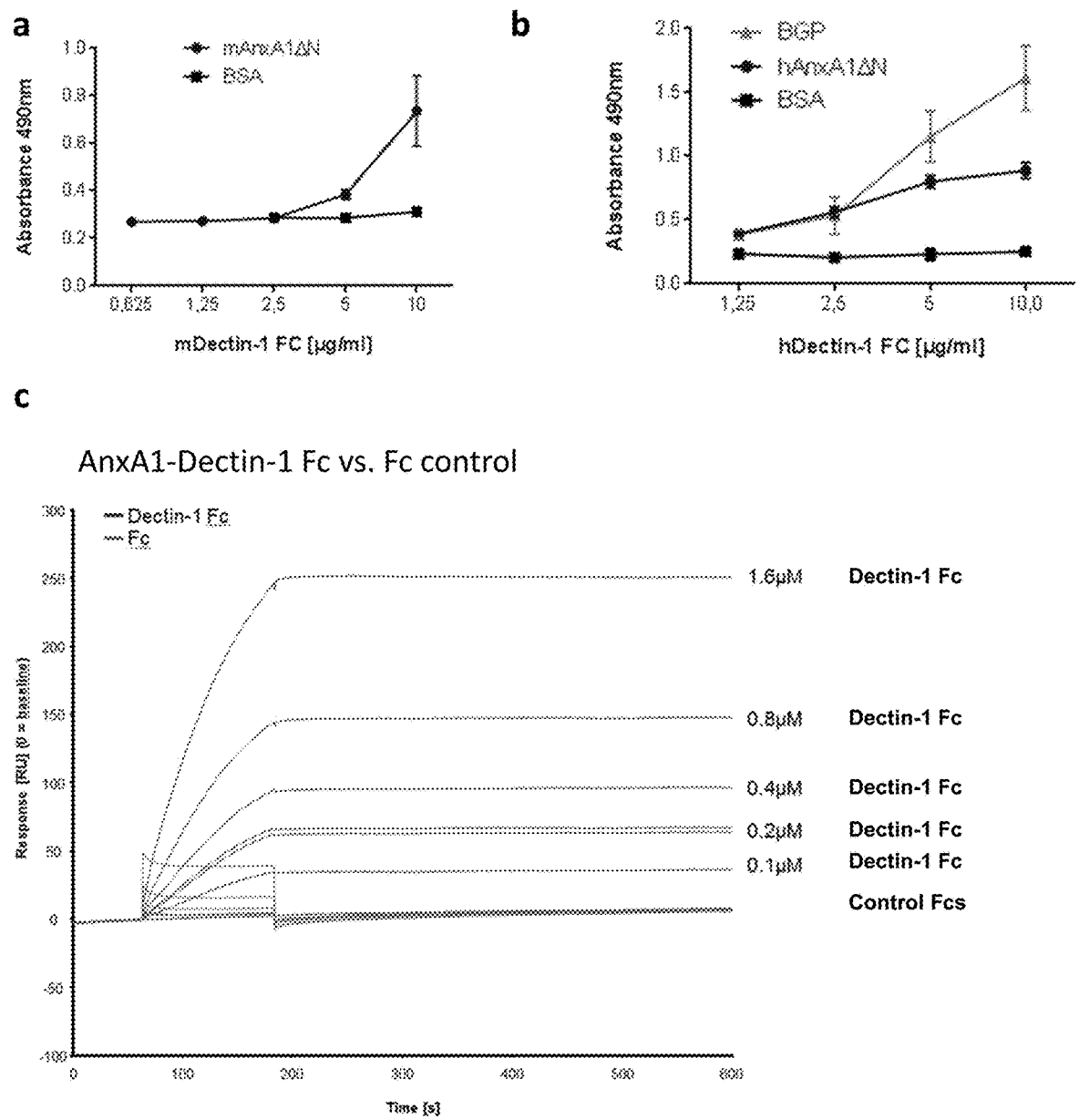

FIG. 7 shows the annexm core domain being recognized by both human and mouse Dectin-1. (a) mAnxA1ΔN or (b) hAnxA1ΔN (10 µg/ml) were coated on 96-well plates under presence of 5 mM CaCl$_2$) overnight. The plates were blocked using PBS/5% BSA supplemented with 5 mM CaCl$_2$) for 1 h. The binding of (a) mDectin-1 and (b) hDectin-1 to plate-bound AnxA1ΔN was detected by an HRP-conjugated mouse anti-hFc antibody. Development was performed with o-phenylenediamine dihydrochloride. Results are representative of at least two independent experiments.

(c-h) SPR-sensograms of Anx/mDectin-1 hFc interaction. Indicated Anx was immobilized on a CM5 Sensor Chip. mDectin-1 hFc and control Fc were used as ligands in flow. The sensograms show only the active flow cell.

Figure 8:
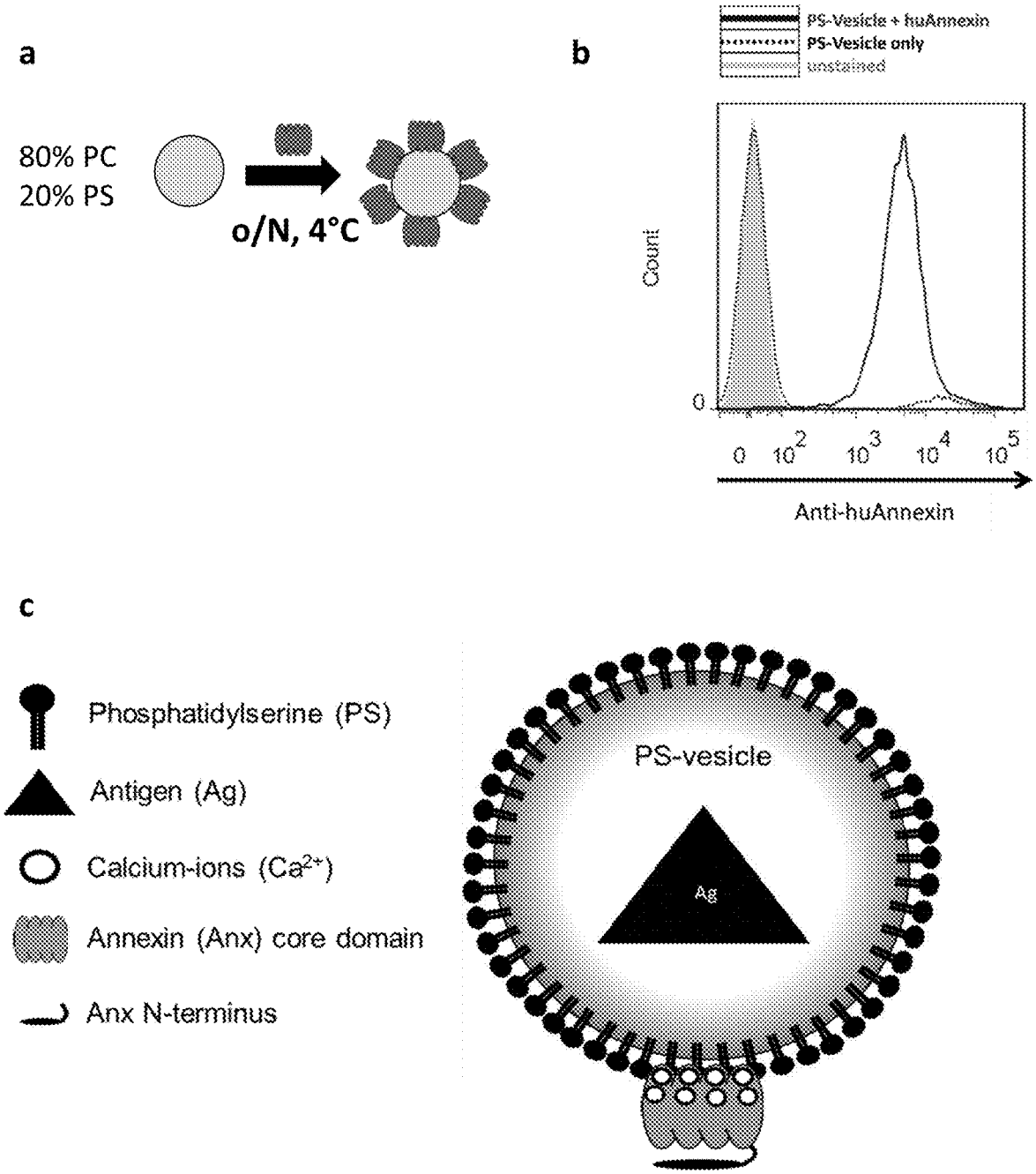

FIG. 8 shows generation of annexin-coated vesicles comprising phosphatidylserine.

(a) Graphical representation of the generation of PS-vesicles coated with hAnxA1ΔN.

(b) Representative flow cytometry analysis of Anx expression on PS-vesicles.

(c) Graphical representation of an exemplary annexin-coated PS-vesicle further comprising an antigen.

Figure 9:
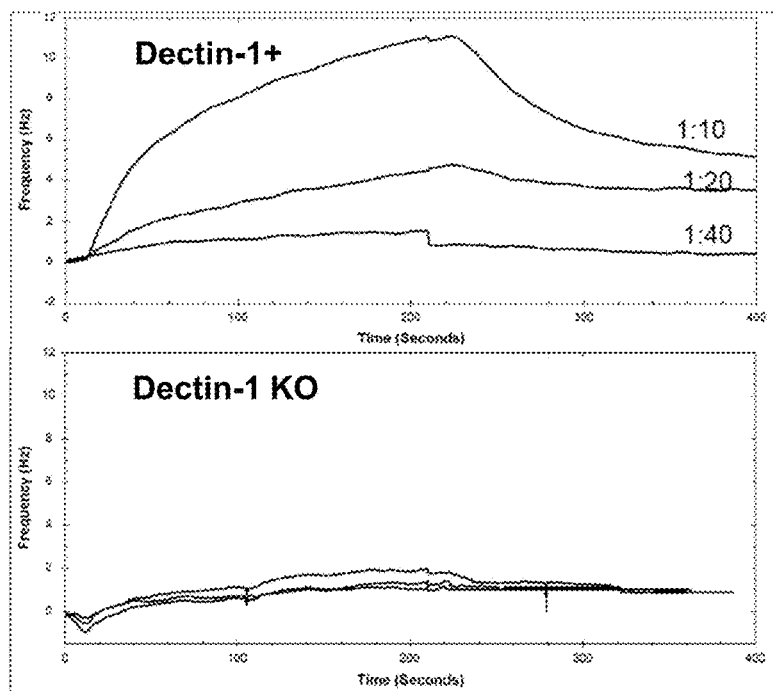
Figure 9:
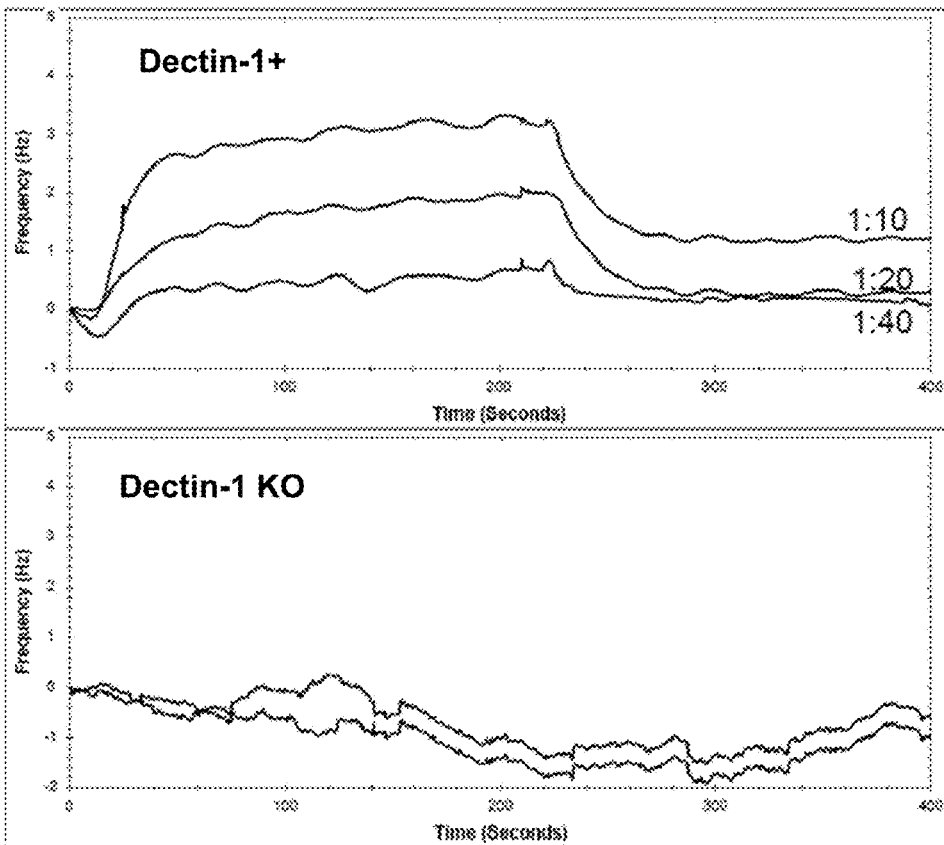

FIG. 9 shows QCM binding analysis of DZ and vesicle-bound hAnxA1AN to MM6 cells. (a and b) human (h) Dectin-1 (hDectin-1) overexpressing and Dectin-1 KO MM6 cells were immobilised on Attana sensor surfaces using the capturing molecule ConA. Interaction of the analytes with cell surfaces was assessed using Attana Cell 200™ biosensor. The signal output is given in frequency (Hz) and is directly related to changes in mass on the sensor surface. (a) QCM-based analysis of Vesicle-bound annexin A1ΔN in different ratios as indicated. (b) QCM-based analysis of filtrated depleted zymosan (DZ) (≤400 nm) in different ratios as indicated. Shown are representative results of two independent experiments.

Figure 10:
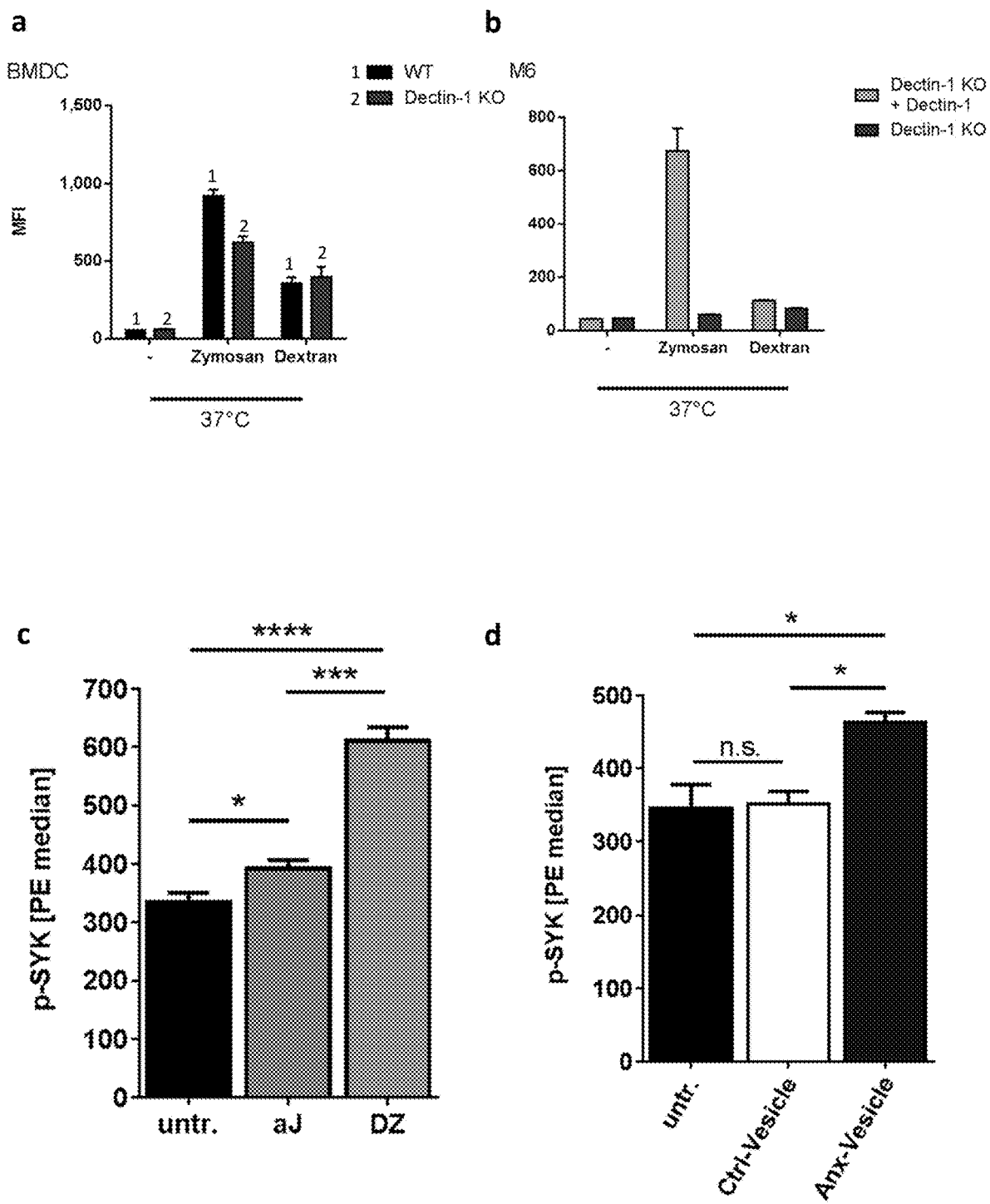

FIG. 10 shows vesicle-bound AnxA1ΔN and ACs inducing Dectin-1-dependent phosphorylation of SYK.

(a and b) Control experiments for Dectin-1-dependent phagocytosis of β-glucans or Dextran as Dectin-1-independent ligand in (a) bone marrow-derived dendritic cells (BMDC) and (b) Mono Mac 6 (MM6) cells. Phagocytosis experiments were analysed after 3 h of incubation on 37° C. or 4° C. as control.

(c and d) SYK-phosphorylation in BMDCs was analyzed by flow cytometry. Cells were treated as indicated under presence of Phosphatase-inhibitor Sodium vanadate (1 mM) and stained on ice with an intracellular antibody against p-SYK.

*$p<0.0001$, *$p<0.001$, *$p<0.05$, n.s.=not significant (unpaired, two-tailed t-test). Results show means±s.d. of one representative experiment out of two to three.

Figure 11:
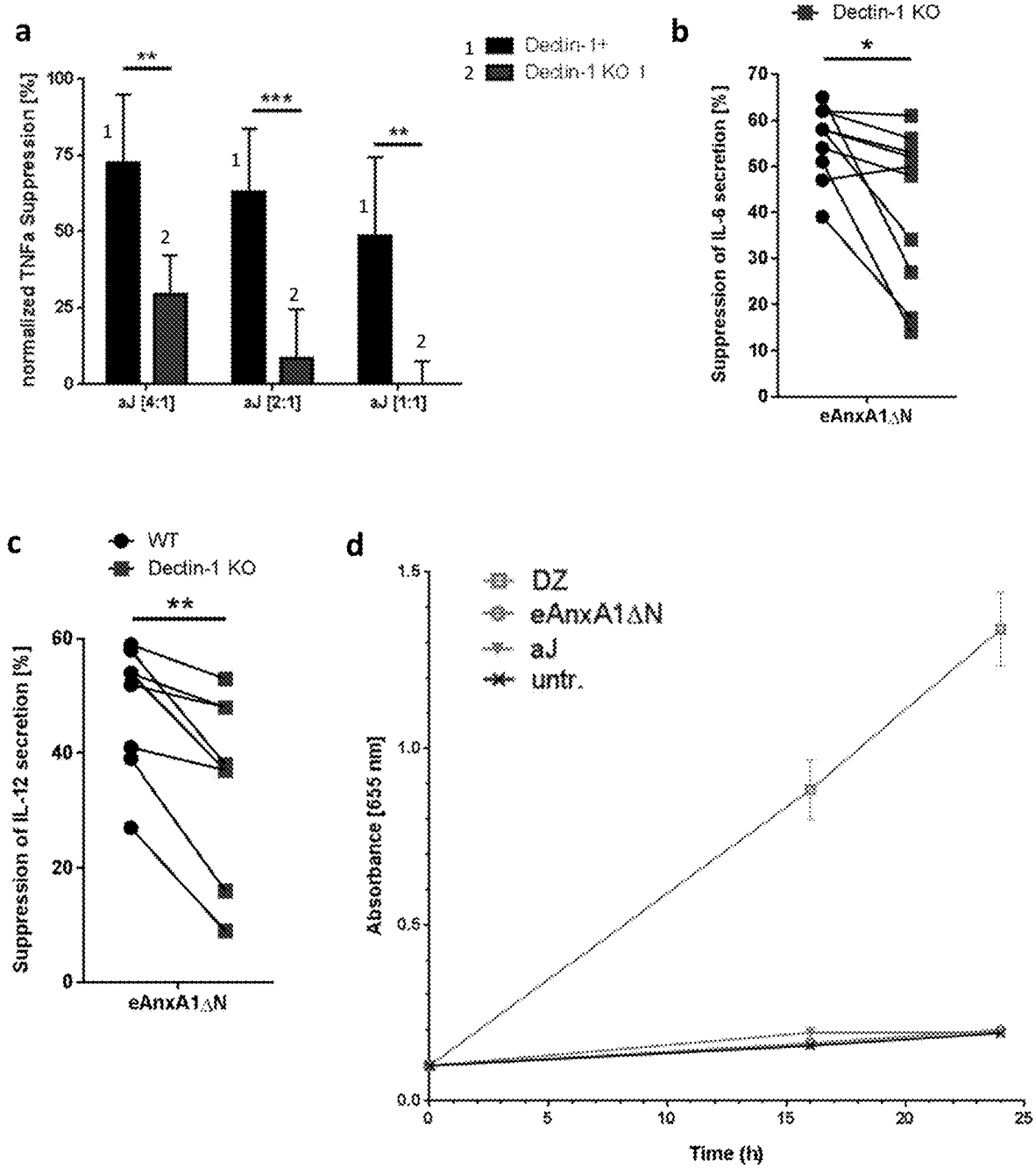

FIG. 11 shows Dectin-1 mediating immunosuppressive effects of apoptotic cells and recombinant AnxA1ΔN.

A total of $10^5$ MM6 cells (a) or BMDCs (b and c) were incubated with eucaryotically expressed mouse (m) annexin (Anx) ALAN (eAnxA1ΔN) (1000 nM) or apoptotic Jurkat T-cells (aJ) in indicated ratios for 8 h. After pre-incubation, cells were stimulated over night with the TLR agonist R848 and 100 µg/ml PMA (a) or with 20-30 nM CpG (b and c). Cytokine concentrations in the supernatants were analyzed by ELISA 24 h after stimulation. The suppression of cytokine secretion is normalized to CpG-stimulation only ((100−treated/CpG only)*100).

Results represent the means±s.d. (a) or the only the means (b and c) out of six to eight independent experiments (a). *$p<0.001$, $p<0.01$, *$p<0.05$ (unpaired (a) or paired (b and c), two-tailed t-test).

d) shows that apoptotic cells and recombinant AnxA1ΔN do not activate NF-κB. Dectin-1 expressing NF-κB reporter cells were treated with indicated ligands overnight. After 16 h and 24 h, activity of secreted embryonic alkaline phosphatase (SEAP) was assessed in the supernatant using QUANTI-Blue™ by reading the optical density (OD) at 655 nm. Results are representative of two independent experiments.

Figure 12:
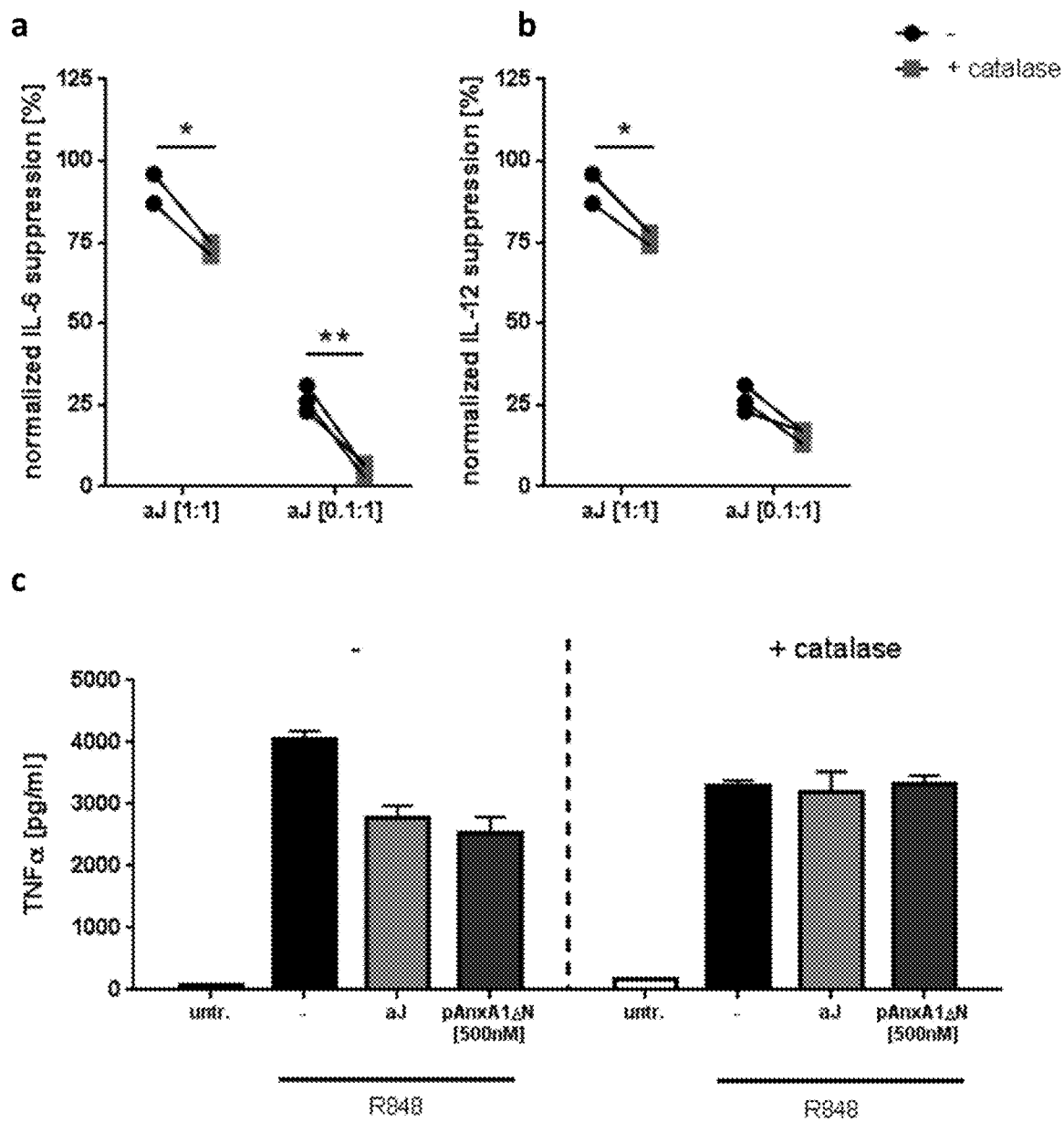

FIG. 12 shows an immunosuppressive effect of annexins on MM6 cells and BMDCs requiring ROS.

A total of $10^5$ (a and b) BMDCs or (c) Dectin-1 expressing MM6 cells were incubated with ROS scavenger catalase or medium for 30 min. Apoptotic Jurkat T-cells (aJ) or pAnxA1ΔN were added and incubated for 8 h. Cells were stimulated overnight with TLR-agonist (a and b) CpG (20-30 nM) or (c) R848 (0.5-1 µg/ml). Indicated cytokines in the supernatants were analyzed by ELISA 24 h after stimulation. (a and b) The suppression of cytokine secretion is normalized to CpG-stimulation only minus untreated (100−((treated−untreated)/(CpG only−untreated)*100). *$p<0.001$, $p<0.01$, *$p<0.05$ (paired, two-tailed t-test). Results represent the means out of two to three independent experiments (a and b). Representative results of at least two independent experiments (c).

Figure 13:
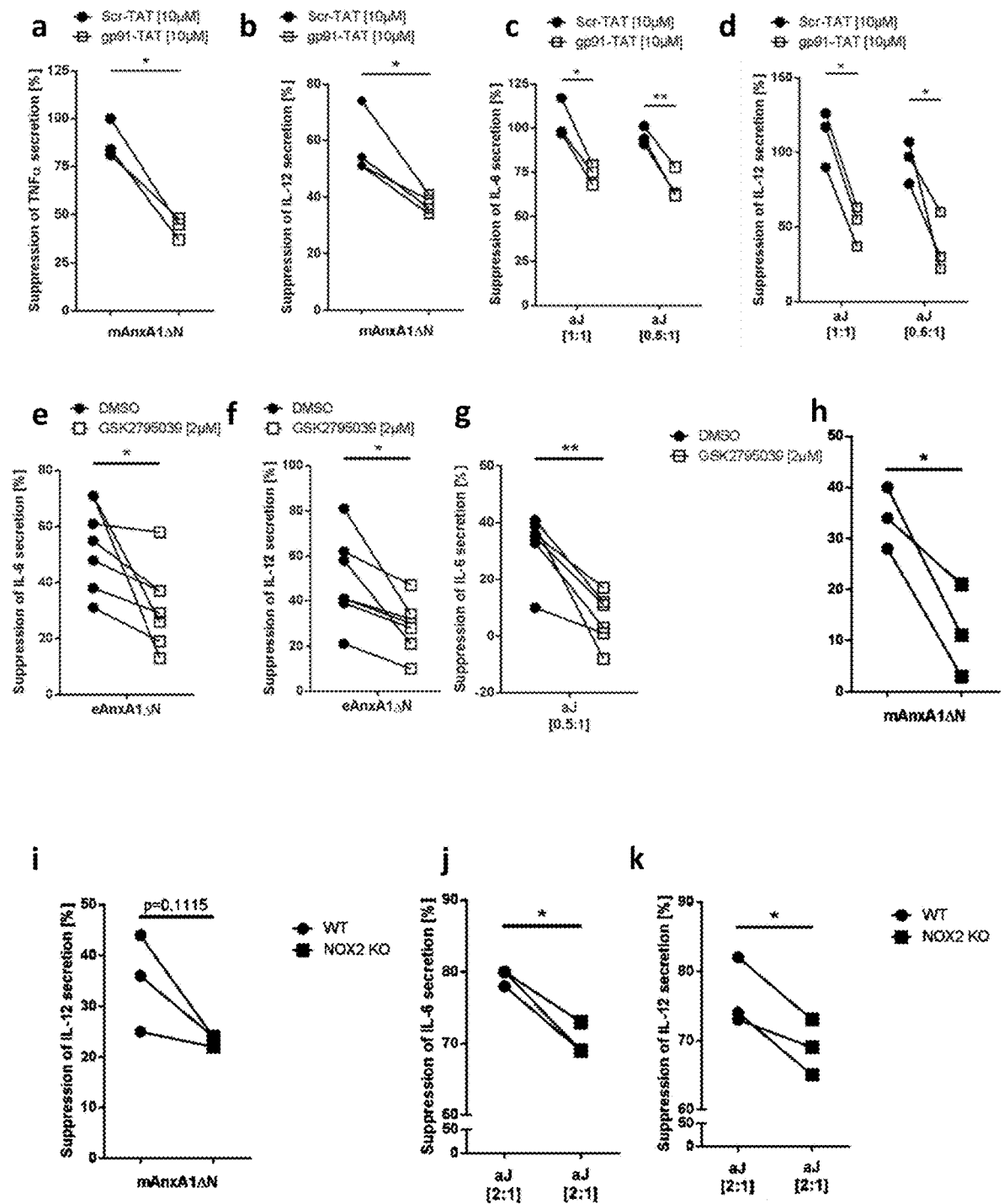

FIG. 13 shows that an effective immunosuppression of AC-derived annexins requires ROS. Quantification of suppression experiments performed as in FIG. 5. WT BMDCs were pre-incubated with NOX-2 inhibitors gp91-TAT (a-d) or GSK2795039 (e-g) for 30 min. Subsequently, apoptotic Jurkat T-cells (aJ; RRID:CVCL_0367; ratio of 0.5:1) or eucaryotically expressed mAnxA1ΔN (1000 nM) were added and BMDCs were further incubated for 8 h. (h-k) BMDCs generated from NOX-2-deficient mice and WT littermate controls were incubated with aJ (ratio of 2:1) or mAnxA1ΔN (500 nM). After pre-incubation, BMDCs were stimulated with TLR-agonist CpG (20-30 nM). Indicated cytokines in the supernatants were analyzed by ELISA 24 h after stimulation. Results represent the means out of three (a, c, d and h-k), four (b) or seven (e-g) independent experiments. *$p<0.001$, $p<0.01$, *$p<0.05$ (paired, two-tailed t-test).

Figure 14:
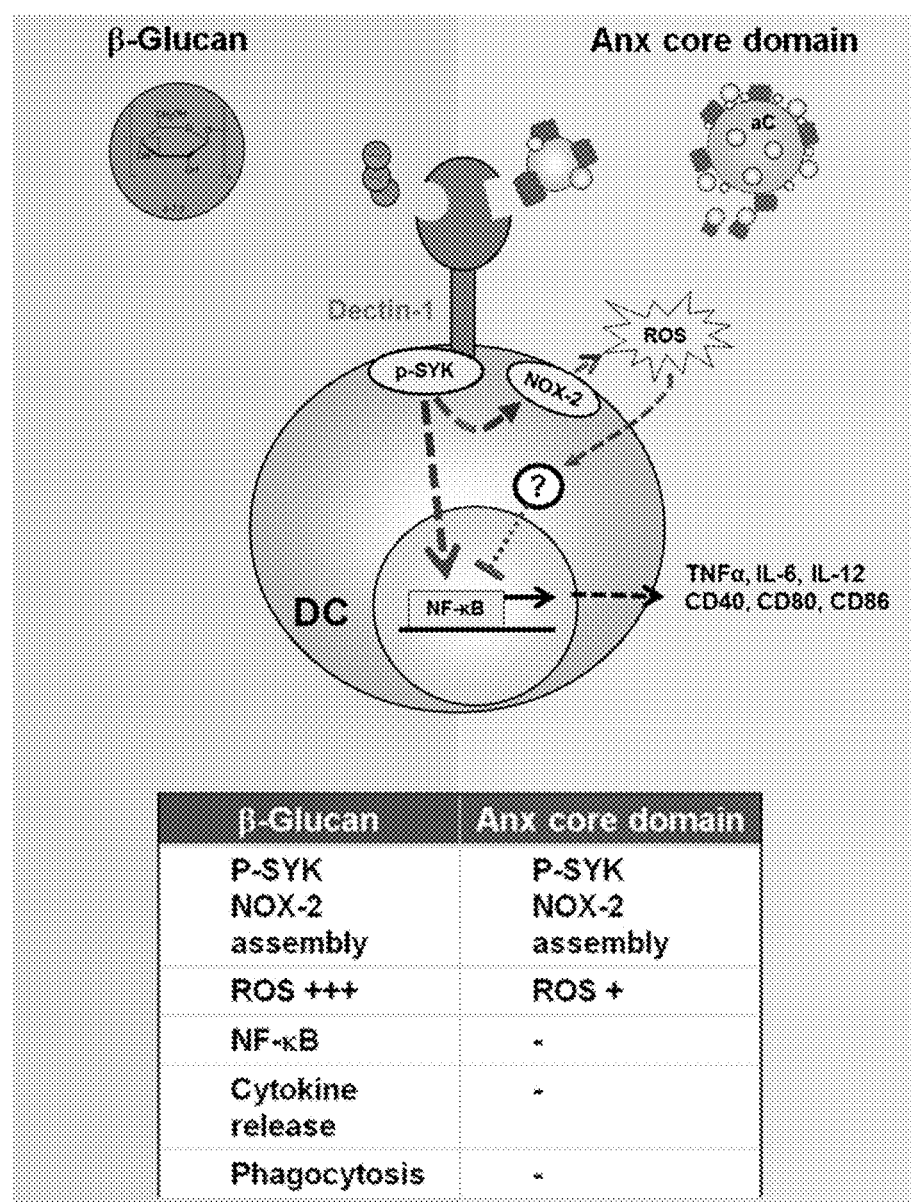

FIG. 14 shows the interaction of pathogen-derived β-glucans and (Anx) ALAN (Anx core domain) on the surface of apoptotic cells with Dectin-1 on distinct recognition sites. Binding of the Anx core domain by Dectin-1 leads to phosphorylation of spleen tyrosine kinase (SYK) and induces a NOX-2-dependent release of reactive oxygen species (ROS) leading to inhibition of dendritic cell (DC)-activation. In contrast to pathogen-derived β-glucans, the Anx core domain does not activate NF-κB.

In the following, reference is made to the examples, which are given to illustrate, not to limit the present invention.

EXAMPLES

Example 1: Production of Annexin Preparations and Dectin Derivatives

Recombinant prokaryotic Anx (pAnx) was expressed using the *Escherichia coli* strain BL21 (DE3) pLysS (Promega) and eukaryotic Anx (eAnx) was produced by the EMBL Protein Expression and Purification Core Facility (Heidelberg, Germany) in Baculovirus infected insect cells. Removal of LPS during protein purification was achieved by washing with TBS containing 0.1% Triton X-114 (SIGMA-Aldrich) and subsequent ion-exchange purification. LPS content in all annexin preparations was determined to be below 0.001 EU/mg using the Limulus amoebocyte lysate assay (Lonza) according to the manufacturer's instructions. Plasmids for human hDectin-1a, hDectin-1b and hDC-SIGN (all Invivogen) were transfected using AMAXA-Nucleofection technology (Lonza). To generate stably transfected MM6 or Jurkat T-cell lines, cells were selected using Blasticidin S Hydrochloride (Fisher Scientific) for 21 to 28 d or, if necessary, got finally separated via FACS using fluorescently labeled anti-Dectin-1 or anti-DC-SIGN Abs after 3 to 14 d of Blasticidin selection. Dectin-1-deficient MM6 cells were generated using CRISPR/Cas9 genome-editing technology.

Example 2: Preparation of Lipid Vesicles

Lipid-vesicles for initial binding experiments were generated by sonication. Phosphatidylcholin (PC, 1,2-dioleoyl-sn-glycero-3-phosphocholine) and phosphatidylserine (PS, 1,2-dioleoyl-sn-glycero-3-phospho-L-serine) (both purchased from Avanti Lipids Polar) were mixed in a 5:1 ratio (PC:PS), supplemented with 50 μg/ml endotoxin-free OVA and solved in Chloroform (≥99.9%, SIGMA-Aldrich). After evaporation using a concentrator 5301 with vacuum degassing equipment (Eppendorf), the dry lipid/OVA-pellet was resuspended with DPBS ($Ca^{2+}$ and $Mg^{2+}$ included; Life Technologies) and sonicated with a SONOPULS HD 2070 device (Bandelin, at Cycle 5, 30% power) for 1 min. Lipid-vesicles were centrifuged for 30 min by 18,000×g at 4° C. After removing the supernatant, lipid-vesicles were resuspended with fresh DPBS.

For preparing annexin-coated lipid vesicles, an aliquot of lipid vesicles diluted 1:5 in DPBS ($Ca^{2+}$ and $Mg^{2+}$ included) were supplemented with hAnxA1ΔN (50 μg/ml) and incubated over night at 4° C. on a roll shaker. Residual annexin was removed by centrifugation for 30 min at 18,000×g and 4° C. and following resuspension with DPBS ($Ca^{2+}$ and $Mg^{2+}$ included). The annexin-loading was analysed using inhouse custom-made fluorescently labeled anti-hAnx-FITC mAb.

Example 3: Preparation of Size-Defined Annexin-Coated Lipid Vesicles

Figure 1:
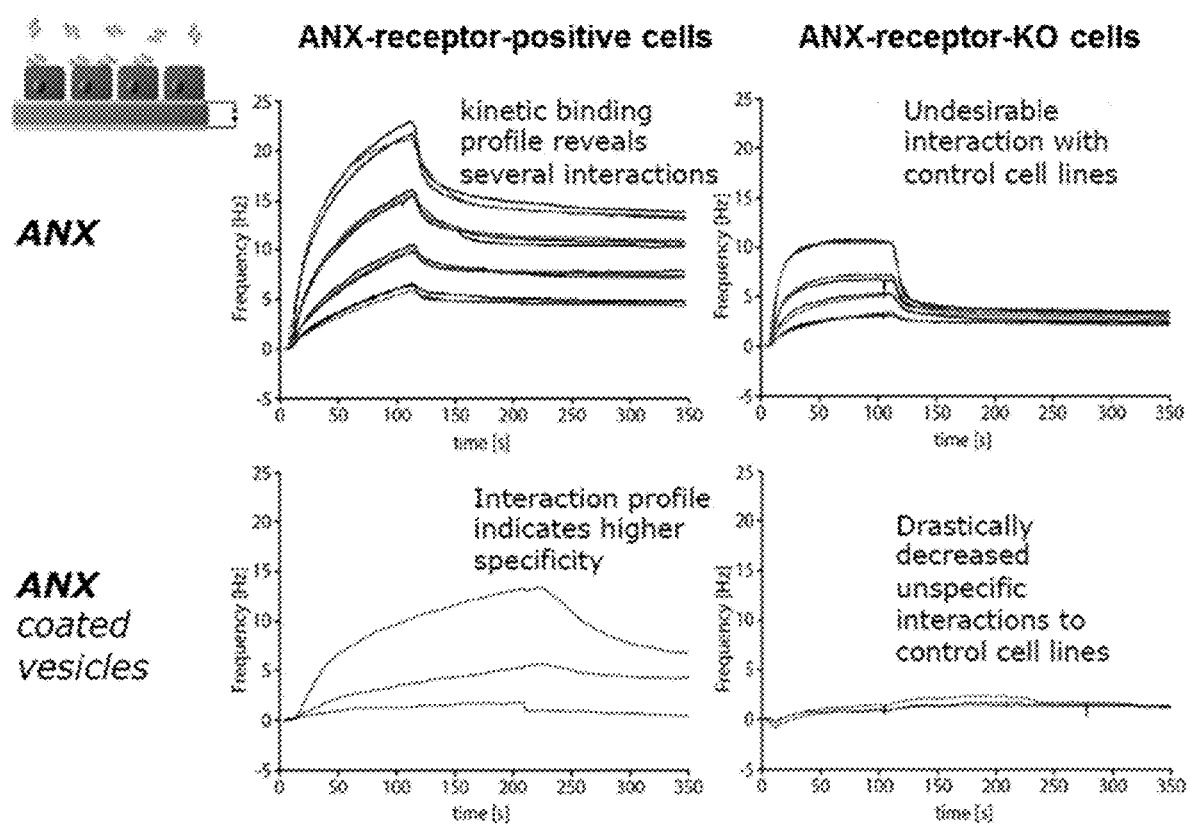
FIG. 1 shows an optimized annexin (ANX) preparation, which is an annexin-coated lipid vesicle, to specifically bind to a proteinaceous target ANX-receptor on cellular surfaces.
Figure 2:
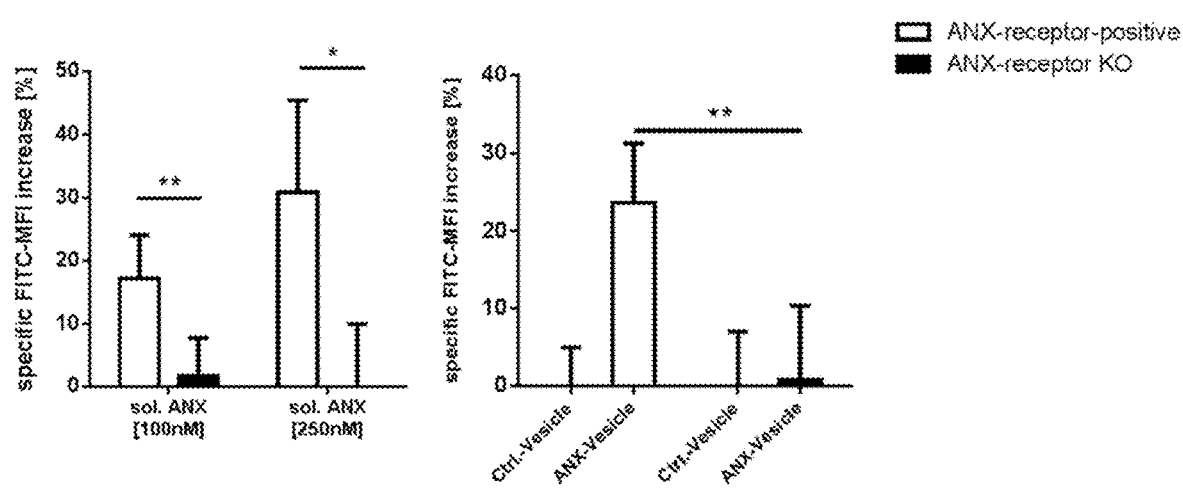
FIG. 2 shows soluble annexin (sol. ANX) and ANX-coated vesicles inducing an ANX-receptor-dependent induction of a second messenger indicated by an increase in FITC-mean fluorescent intensity (MFI). *p<0.5, **p<0.01 (unpaired, student's t-test)
Figure 3:
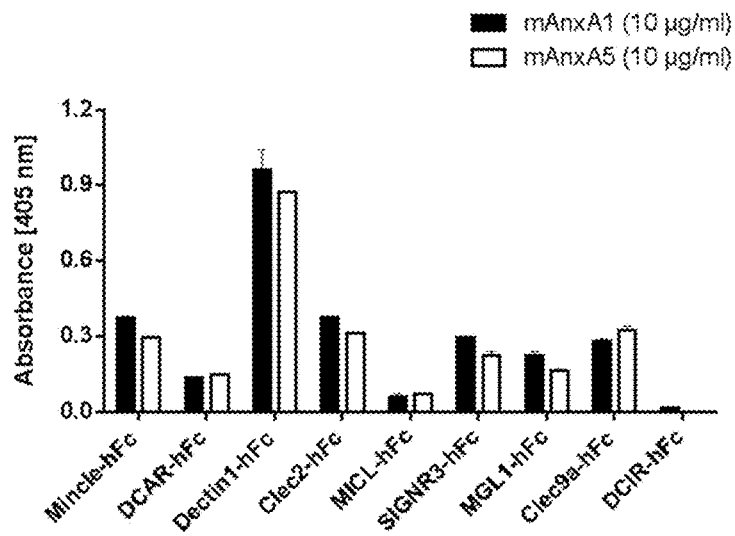
FIG. 3 shows that the conserved annexin core domain is recognized by Dectin-1 at sites distinct from β-glucan binding sites.
(a) Mouse (m) annexin (Anx) A1 and mAnxA5 were immobilized and incubated with the indicated C-type lectine receptor (CLR) human (h) Fc fusion proteins (CLR-hFc). Fusion proteins were detected using an alkaline phosphatase (AP)-conjugated anti-hFc antibody.
(b) Interaction of depleted zymosan (DZ) or hAnxA1ΔN-coated vesicles with hDectin-1 expressing and Dectin-1 KO MM6 cells using QCM-technology. Both cell types were immobilised on Attana sensor surfaces using the capturing molecule ConA. Interaction of the analytes with cell surfaces was assessed using Attana Cell 200™ biosensor. The signal output is given in frequency (Hz) and is directly related to changes in mass on the sensor surface.
(c) Characteristic binding responses of filtrated DZ (≤400 nm) and hAnxA1ΔN-coated vesicles to hDectin-1 expressing MM6 cells. The $B_{max}$ value indicates the ligand specific frequency of fully saturated cell-surface binding (DZ≈7 Hz, hAnxA1ΔN-coated vesicles≈14 Hz).
(d) First, DZ was applied to the immobilized cells several times (undotted arrows) until full binding response of DZ (≈7 Hz) to the cell surface was obtained. Next, a mixture of DZ and hAnxA1ΔN-coated vesicles was applied several times (dotted arrows) to investigate the occurrence of an additional binding response.
(e) Competition experiments as described in (d) but analytes were applied in reverse order (dotted arrows: injection of hAnxA1ΔN-coated vesicles, undotted arrows: injection of DZ and hAnxA1ΔN-coated vesicles). Results are representative of at least two independent experiments.
Figure 3:
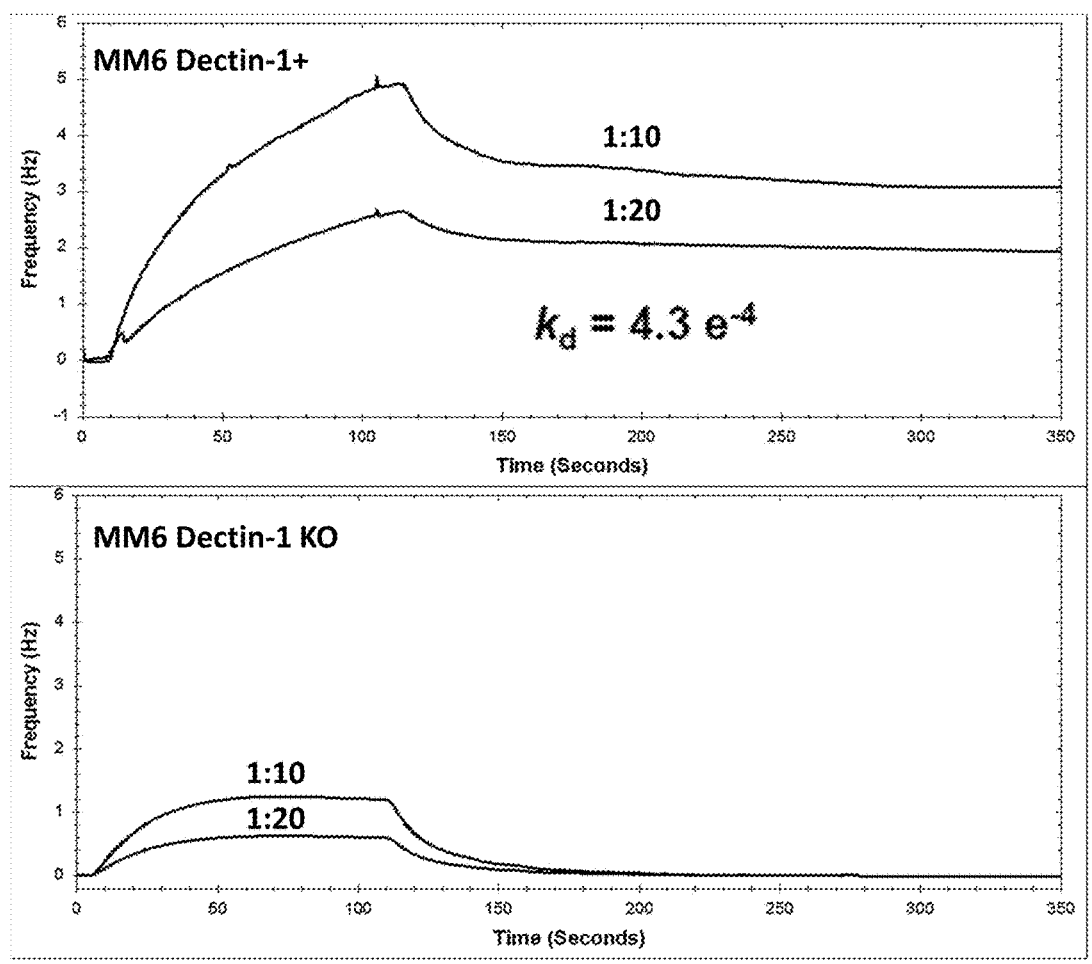

Size defined phosphatidylserine (PS)-containing lipid-vesicles for competition experiments (FIG. 3c-e) were generated by extrusion adapted from W. Nickel et al. [11]. 18:1 (D9-Cis) phosphatidylcholine (DOPC), 18:1 PS (DOPS) and Cy5-labeled phosphatidylethanolamine (Cy5-PE) (all from Avanti Polar Lipids) dissolved in chloroform (SIGMA-Aldrich) were mixed in a molar ratio of 79% DOPC, 20% DOPS and 1% Cy5-PE in a 10 ml glass round-bottom flask, which had been washed with detergent, deionized water, methanol and three times with chloroform. The lipids were pipetted with Hamilton syringes in order to prevent chloroform-mediated plastic contaminations. The lipid mixture was dried under vacuum in an Eppendorf concentrator without centrifugation for approximately 2 h, until all chloroform had evaporated. The remaining lipid layer was dissolved in 50° C. pre-warmed PBS containing 10% sucrose by short-time vortexing while keeping the temperature at 45-50° C. in a water bath. Next, the lipid solution was frozen in liquid nitrogen and subsequently thawed in a water bath until the lipid solution became completely liquid again. In order to exclude the formation of multi-lamellar liposomes, ten of such freeze/thaw-cycles were performed. The extruder was assembled with a 400 nm pore-size membrane and the 45° C. pre-warmed lipid solution was pushed through the membrane 21 times. The homogenized lipid mix was then collected in 1.5 ml reaction tubes and the synthetized liposomes were washed twice by adding DPBS without sucrose and centrifugation at 18,000×g for 20 min at 4° C. The lipid-vesicles were stored at −80° C. until use. For preparation of annexin-coated vesicles 200 μl of lipid-vesicle stock solution diluted 1:5 in DPBS ($Ca^{2+}$ and $Mg^{2+}$ included) was supplemented with the human annexin A1 core domain (said core domain being prepared as described previously [4], 50 μg/ml) and incubated over night by 4° C. on a roll shaker. Residual annexin was removed by centrifugation for 90 min at 18,000×g on 4° C. and following resuspension with 200 μl DPBS ($Ca^{2+}$ and $Mg^{2+}$ included). The annexin-loading was analysed using fluorescently-labeled anti-hAnx-FITC mAb (DAC5) [3].

Example 4: The C-Type Lectin Receptor Dectin-1 Binds to the Conserved Annexin Core Domain Specific receptor binding to various annexin family members was evaluated by testing binding of recombinant annexin A1 and annexin A5 in parallel to a C-type lectin receptor (CLR)-Fc library.

A library of CLR-Fc fusion proteins was prepared. Briefly, murine splenic RNA was reverse transcribed into cDNA using Reverse Transcriptase (New England Biolabs). The cDNA encoding the extracellular part of each CLR was amplified by polymerase chain reaction (PCR) and was then ligated into the pFuse-hIgG1-Fc expression vector (Invivogen). The CLR-Fc vector constructs were either stably transfected into CHO cells or transiently transfected using the FreeStyle Max CHO-S Expression System (Life Technologies). Purification of the CLR-Fc fusion proteins from the cell supernatant was performed using HiTrap Protein G HP columns (GE Healthcare). The purity of each CLR-Fc fusion protein was confirmed by sodium dodecyl sulfate polyacrylamide gel electrophoresis (SDS-PAGE) and subsequent Coomassie staining, Western Blot using anti-human IgG-HRP antibody (Dianova) as well as mass spectrometry. mAnxA1 (0.5 µg/well) and mAnxA5 (0.5 µg/well) were coated on 96-well high binding plates (Greiner) overnight. After blocking with 1% BSA in PBS, 20 µg/mL of each CLR-Fc fusion protein was incubated in lectin binding buffer (50 mM HEPES, 5 mM $MgCl_2$, 5 mM $CaCl_2$, pH 7.4) at RT for 2 h. The binding of CLR-Fc fusion proteins was detected by an alkaline phosphatase-conjugated goat anti-hFc antibody (Dianova). Development was performed with p-nitrophenyl phosphate (Thermo Scientific).

Of all CLRs tested, specific binding to both annexins was only detected for Dectin-1 (FIG. 3a). Since all annexin family members share the annexin core domain, these data suggest that Dectin-1 binds to the conserved annexin core domain. The specific binding of Dectin-1 to the annexin A1 core domain was confirmed by using a truncated version of annexin A1 (annexin A1ΔN) lacking the N-terminus (FIGS. 7a and b).

Moreover, Fc-receptor based surface plasmon resonance experiments were performed. Surface Plasmon Resonance (SPR) binding analyses were carried out on a Biacore T100 instrument (GE Healthcare). CM5 sensor chips were functionalized with about 10,000 RUs of AnxA1 using the Amine Coupling Kit (GE Healthcare) according to the manufacturer's recommendations. Kinetic measurements were performed with the Biacore T100 Control software using the 'Kinetics' function. HEPES (10 mM) containing $CaCl_2$ (1 mM), $MgCl_2$ (1 mM), 0.005% Tween pH 7.4 was used as running buffer and all measurements were performed at 25° C. and a flow rate of 30 µl min$^{-1}$. About 500 RUs of fusion proteins were captured and the indicated concentrations were passed through, using the standard parameters for association and dissociation times. Flow cells were regenerated with 10 mM glycine-HCl pH 1.7 for 30 s. Kinetic evaluation of binding responses was performed with the Biacore T100 Evaluation software. Surface plasmon resonance experiments showed high affinity-binding of Dectin-1 to all annexins tested (annexin A1, annexin A1ΔN, annexin A5 and annexin A13) in a nanomolar range (FIG. 7c-h).

In order to investigate the Dectin-1/annexin interaction in a more physiological context, cell-based binding affinity measurements were performed using quartz crystal microbalance (QCM) technology. In contrast to conventional systems, the cell-based QCM technology allows the study of interactions in a physiological cell surface environment and relates changes in mass to a difference in frequency of the sensor. In brief, Dectin-1 expressing and Dectin-1 KO MM6 cells were immobilised on Attana sensor surfaces using a capturing approach. Cell pellets were washed and resuspended in PBS to a final density of 2×10$^6$ cells/ml. Immobilization of capturing molecule Concanavalin A (ConA) on LNB carboxyl surfaces (3623-3001) was performed using Attana amine coupling kit (3501-3001). 150 Hz of ConA was stably immobilized on the surfaces. Cells were captured on surfaces by incubating 10$^5$ cells in PBS for 30 min at RT. Following incubation, the cells were rinsed three times with 0.7 ml PBS at RT and stabilized in fresh 4% (v/v) methanol-free formaldehyde (Thermo Fisher Scientific) for 15 min at 4° C. Cell coverage was determined by staining cells with 3 µM DAPI (Merck) and visualized under fluorescent microscope. Interaction of the analytes with cell surfaces was assessed using Attana Cell 200™ biosensor. Initial binding experiments were performed at a flow rate of 20 µl/min at 22° C. The blank injection was subtracted from the subsequent analyte injection to correct for baseline drift. One analyte at a time was injected for 105 s over cell surfaces. For kinetic experiments, four two-fold dilutions of each analyte were injected over cell surfaces. Surface regeneration was carried out using a 30 s injection of glycine 10 mM (pH 2.2). Repeated injections of the same analyte concentration resulted in identical binding curves, indicating that regeneration did not alter the binding capacity of the surface. For competitive binding analysis the cells were coated on the sensor surface as described above. The experiments were performed at a flow rate of 20 µl/min at 22° C. during continuous flow of PBS. Single cycle kinetic experiments were performed to determine the saturation levels ($B_{max}$ values) of each analyte for the given surface. hAnxA1ΔN-coated vesicles were injected into the flow cell over Dectin-1-expressing MM6 cells until saturation ($B_{max}$). A mixture of hAnxA1ΔN-coated vesicles and DZ (1:1) was further injected over the saturated surface. Experiments were also performed in the reverse order, i.e. injecting DZ before the mixture. The frequency change in the sensor surface resonance (ΔF) during the binding experiments was recorded using the Attester software (Attana AB) and the data was analysed using the Evaluation (Attana AB) and TraceDrawer software (Ridgeview Instruments) using 1:1 or 1:2 binding models to calculate the kinetic parameters including the rate constants (ka, kd), dissociation equilibrium constant (KD) and the maximum binding capacity (Bmax).

Stably transfected Dectin-1 expressing human monocytic Mono Mac 6 (MM6) cells and CRISPR-Cas9 mediated Dectin-1 knock-out (KO) MM6 cells were used for testing, as well as soluble recombinant annexin A1ΔN and annexin A5 as ligands, and a Dectin-1 specific antibody and the specific Dectin-1 ligand depleted zymosan (DZ) as positive controls. Stronger binding of annexins to Dectin-1 expressing MM6 was observed compared to the Dectin-1 KO MM6 cells (Tables 1 and 2). However, affinities to Dectin-1 could only be calculated by deducing the background binding to Dectin-1 KO cells. Background binding of annexins to negatively charged phospholipids like phosphatidylserine (PS) expressed at low levels on cell surfaces of living phagocytes was observed in Dectin-1 KO cells (Tables 1 and 2, FIG. 3).

TABLE 1

AnnexinA1ΔN binding to Dectin-1+ and Dectin-1 KO MM6 cells using cell-based Quartz Crystal Microbalance (QCM) technology.

| Cell type | $k_{a1}$ ($10^3 M^{-1}s^{-1}$) | $k_{d1}$ ($10^{-3}s^{-1}$) | $K_{D1}$ (nM) | $B_{max1}$ (Hz) |
|---|---|---|---|---|
| Dectin-1+ cells | 4.3 | 2.0 | 450 | 103 |
| Dectin-1 KO cells | 4.1 | 3.0 | 720 | 39 |
| ChA-ChB | 4.1 | 1.7 | 408 | 80 |

TABLE 2

AnnexinA5 binding to Dectin-1+ and Dectin-1 KO MM6 cells using cell-based Quartz Crystal Microbalance (QCM) technology.

| Cell type | $k_{a1}$ ($10^4 M^{-1} s^{-1}$) | $k_{d1}$ ($10^{-4} s^{-1}$) | $K_{D1}$ (nM) | $B_{max1}$ (Hz) |
|---|---|---|---|---|
| Dectin-1+ cells | 10 | 3.2 | 3.2 | 15 |
| Dectin-1 KO cells | 33 | 7.4 | 2.3 | 3.0 |
| ChA-ChB | 8.9 | 6.3 | 7.1 | 13 |

TABLE 3

Binding of an αDectin-1 mAB to Dectin-1+ and Dectin-1 KO MM6 cells using cell-based Quartz Crystal Microbalance (QCM) technology.

| Cell type | $k_{a1}$ ($10^3 M^{-1} s^{-1}$) | $k_{d1}$ ($10^{-4} s^{-1}$) | $K_{D1}$ (nM) | $B_{max1}$ (Hz) |
|---|---|---|---|---|
| Dectin-1+ cells | 1.3 | 2.0 | 150 | 18 |
| Dectin-1 KO cells | | no interaction | | |

The data disclosed herein identify the CLR Dectin-1 as an immunosuppressive signalling receptor on the surface of target cells such as early ACs, which is bound by annexins, i.e. soluble annexin and/or annexin-coated particles of the present invention. The recognition site of annexin A1ΔN on Dectin-1 is herein disclosed to be distinct from its β-Glucan binding site and to be still available for dectin-1 binding even if the phospholipid-binding site of annexin is bound to a phospholipid. A nanomolar affinity of vesicle-bound annexin A1ΔN to Dectin-1 was detected, which is similar to the affinity of the inhibitory Dectin-1 ligand laminarin.

Example 5: Reducing Background Binding by Pre-Adsorbing Annexin

To prevent the background binding of annexins to negatively charged phospholipids, PS-containing lipid vesicles were prepared and loaded with annexin A1ΔN (FIGS. 8a and b). This way, the putative receptor binding interface of annexins—as present e.g. on apoptotic cells—was still available for interaction while the PS-binding sites were occupied. Using annexin-coated lipid vesicles, the present inventors demonstrated distinct binding to Dectin-1 expressing MM6 cells with an apparent $k_d$-value of $4.3e^{-4}$ comparable to the anti-Dectin-1 monoclonal antibody (Acris) (FIG. 3b and table 3). Conclusively, Dectin-1 is a specific receptor for the PS-bound core domain of annexin A1 and other annexin family members.

Furthermore, competition QCM experiments were performed to investigate whether or not annexins share the same binding site with classical pathogen-derived Dectin-1 ligands such as DZ. In these experiments, exclusive binding to Dectin-1 expressing MM6 cells, as compared to Dectin-1 KO MM6 cells, was observed (FIGS. 9a and b). The specific change of frequency for saturation of both ligands (14 Hz for annexin A1ΔN and 7 Hz for DZ on Dectin-1 expressing MM6 cells, FIG. 3c) was determined. For competition experiments, Dectin-1 expressing MM6 cells were saturated with DZ and any additional changes in frequency upon subsequent injections of vesicle-bound annexin A1ΔN was measured. Data shown in FIG. 3d demonstrate that vesicle-bound annexin A1ΔN was still able to bind to DZ-saturated cells with kinetics identical to vesicle-bound annexin A1ΔN alone (FIG. 3c). These results were reproduced by injecting the ligands in reversed order (FIG. 3e). In summary, the data show that the lipid-bound annexin A1 core domain binds to a distinct binding site of Dectin-1 not interfering with the binding of pathogen-derived β-glucans.

Example 6: Annexin Induces Dectin-1-Dependent SYK-Phosphorylation and Production of Reactive Oxygen Species (ROS)

Dectin-1 is a well-known receptor for internalization of fungi with exposed cell wall β-glucans. To test an involvement of Dectin-1 in the uptake of apoptotic cells, or efferocytosis, phagocytosis experiments were performed with bone marrow-derived dendritic cells (BMDC) and MM6 cells. For induction of apoptosis, cells were irradiated with 75 mJ/cm² (Jurkat T-cells) or 500 mJ/cm² (RMA-OVA cells) UV-C in a Stratalinker 1800 (Stratagene/Agilent Technologies) and used after 2-2.5 h of incubation in RPMI/10% FCS at 37° C. Surprisingly, efferocytosis was only marginally decreased in Dectin-1-deficient cells (FIGS. 10a and b).

The present inventors disclose that the recognition site of annexin on Dectin-1 is distinct from Dectin's β-glucan binding site. In accordance with the unique binding site and in contrast to Dectin-1-dependent phagocytosis of β-glucans, the present inventors did not detect a prominent role for the Decin-1-annexin interaction in phagocytosis or efferocytosis. The present inventors conclude that receptors other than Dectin-1 suffice for efficient efferocytosis.

Figure 4:
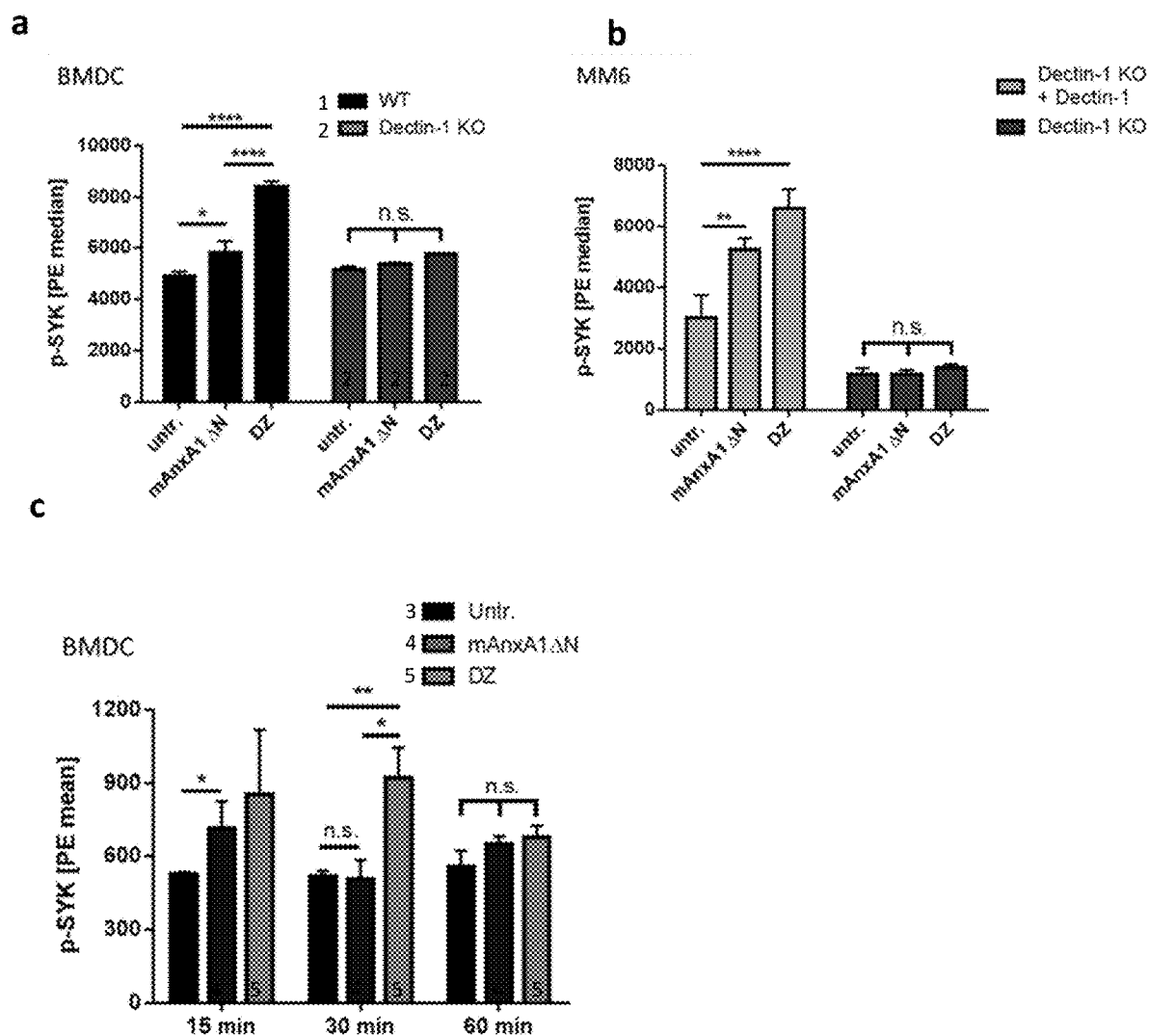
FIG. 4 shows that Annexin induces Dectin-1-dependent SYK-phosphorylation and production of reactive oxygen species (ROS).

One of the earliest signalling events after Dectin-1 activation is the phosphorylation of SYK by Src family kinases. To test whether the annexin core domain also initiates Dectin-1 dependent SYK phosphorylation, an antibody recognizing intracellular SYK-phosphorylation on Tyr348 indicating fully activated SYK was used. In MM6 and primary BMDCs, soluble annexin A1ΔN induced SYK phosphorylation depending on expression of Dectin-1 (FIG. 4a). Phosphorylation of SYK was also observed after treatment with vesicle-bound annexin A1ΔN and apoptotic cells (ACs) (FIG. 10). Surprisingly, the kinetics of SYK-phosphorylation were different between annexin A1ΔN and β-glucans. While DZ induced a long lasting SYK-phosphorylation (≥30 min), annexin-mediated SYK-phosphorylation was characterized by a short peak after 15 min, which declined quickly to baseline levels (FIG. 4b).

One major signalling event after Dectin-1 engagement and SYK-phosphorylation is the generation of ROS. Therefore, cellular ROS-levels after stimulation with annexin A1ΔN were determined. Intracellular amounts of ROS in BMDCs, MM6 and Jurkat T-cells were determined using ROS sensitive $H_2DCFDA$ (SIGMA-Aldrich). $1 \times 10^5$ cells/well were seeded in RPMI/FCS, supplemented with 50 µg/ml of Polymyxin-B (PmxB; Abcam) to exclude LPS-mediated effects. Treatments were added 1 h later and cells were incubated for 0 to 2.5 h at 37° C. Following treatment, 5 µM of $H_2DCFDA$ was added for 0.5 h. The reaction was stopped by addition of 25 µM of hydroxyl radical scavenger Trolox or 20 mM of antioxidant N-Acetyl-L-cysteine (NAC; SIGMA-Aldrich) for 10-15 min. Afterwards, cells were kept on ice in the dark and washed with ice cold RPMI/FCS to slow down cell metabolism supplemented with 100 µM Trolox or 20 mM NAC to exclude unspecific ROS signals during the measurement. ROS production was quantified by flow cytometry within the FITC-channel. The indicated Mean Fluorescence Intensity (MFI)-increase was normalized to untreated cells ((MFI treated−MFI untreated)/MFI untreated*100).

A time dependent increase of ROS-production reaching its maximum after 2 h was detected. Using BMDCs and MM6 cells, the present inventors demonstrated that annexin-mediated generation of ROS is clearly a Dectin-1-dependent effect, observed after treatment with soluble and vesicle-bound annexin A1ΔN or annexin A5, respectively (FIGS. 4c, d and e). The specificity of these assays was further tested by using heat-inactivated annexin as well as the specific ROS-scavenger Trolox (FIG. 4c). Consistently, reconstitution of Dectin-1 expression in Dectin-1 KO MM6 cells was able to rescue the annexin-mediated phenotype with respect to ROS production. The Dectin-1 dependency of annexin-mediated ROS production was validated using intrinsically Dectin-1-deficient Jurkat T-cells stably transfected with Dectin-1 or DC-SIGN as control. Also in this system, treatment with annexin A1ΔN induced a significant ROS-increase in a Dectin-1 specific manner. Dectin-1 independent ROS induction by Phorbol-12-myristat-13-acetate (PMA) was unaltered in all cellular systems. Inhibition of SYK-phosphorylation abrogated the annexin A1ΔN-mediated ROS increase, indicating that annexin A1ΔN induces a SYK-dependent ROS signal (FIG. 4f). Conclusively, these data show that the annexin A1 core domain and annexin A5 serve as endogenous ligands for the C-type lectin receptor (CLR) Dectin-1 leading to SYK-phosphorylation and ROS production. In comparison to the oxidative burst provoked by PMA in BMDCs, annexin treatment induced moderate ROS levels, indicative of a role in signalling cascades (FIGS. 4c and d).

Recognition of annexin A1ΔN by Dectin-1 led to phosphorylation of SYK and induced a NOX-2-dependent release of ROS. However, annexin A1ΔN-induced intracellular ROS levels were substantially lower than ROS levels characteristic for an oxidative burst. Therefore, the data point to the fact that annexin A1ΔN-induced ROS-levels do mainly serve to inhibit intracellular signalling pathways and serve to prevent DC-activation.

Example 7: Annexin-Induced ROS are NADPH Oxidase-2-Dependent

Within cells, ROS are generated by different cellular sources localized in the cytosol, in peroxisomes, at membranes of mitochondria, and at the plasma membrane. The main source of ROS in phagocytes is the plasma membrane-bound enzyme complex NADPH oxidase-2 (NOX-2) which releases ROS into the extracellular environment. In a first attempt to characterize the source of annexin-induced ROS the present inventors aimed at scavenging extracellular ROS by using the membrane impermeable enzyme catalase. Indeed, addition of catalase to the medium abrogated the annexin-mediated ROS-production. Thus, the present inventors considered membrane-bound NOX enzymes as likely candidates for the source of annexin-mediated ROS. To further clarify the involvement of NOX the present inventors additionally used the NOX inhibitor Diphenyleneiodenium (DPI). As observed for catalase, pre-treatment with DPI blocked annexin-induced ROS.

To specifically target NOX-2, the present inventors used the peptide inhibitor gp91-TAT that competitively inhibits NOX-2 assembly but not the activation of other NOX enzymes. In accordance with a role of NOX-2 in annexin signalling, gp91-TAT significantly reduced annexin-induced ROS-production compared to the control peptide Ser-TAT. Finally, the present inventors performed ROS experiments in BMDCs deficient for the main subunit of the NOX-2 complex, gp91 ($gp91^{phox(-/-)}$ mice) and compared them with BMDCs from WT littermates. The ROS signal of annexin was abrogated in $gp91^{phox(-/-)}$ BMDCs. However, stimulation by the NOX-independent ROS-inducer Rotenon remained unaffected. The present inventors also observed significantly enhanced secretion of pro-inflammatory cytokines such as IL-6 and IL-12 by Dectin-1 stimulated $gp91^{phox(-/-)}$ BMDCs, illustrating the inhibitory function of NOX-2-derived ROS. Conclusively, these experiments identified NOX-2 as critical mediator of annexin-mediated ROS-production after binding to Dectin-1.

Surprisingly, not all hallmarks of Dectin-1 signalling following stimulation by β-glucans were initiated by annexin. For instance, annexin did not activate the transcription factor NF-kB or induce inflammatory cytokine secretion, respectively (FIG. 11d). These results imply that annexin exhibits a "biased agonism" with respect to Dectin-1 as observed for several G-protein-coupled receptor-ligand systems, selectively activating inhibitory Dectin-1 signalling events.

An essential role for NOX-2-derived ROS in AC- and annexin-mediated DC-inhibition was detected by the present inventors. The AC- and annexin-mediated DC-inhibition was not completely abrogated in Dectin-1 KO BMDCs. This suggests that additional receptors known to signal via NOX-2 might also contribute to the inhibitory mechanism described here. Nevertheless, the molecular pathway of annexin, i.e. stimulating Dectin-1 and inducing cellular inhibition of target cells such as DCs via NOX-2-derived ROS, represents a novel mechanism of peripheral immune tolerance. Therapeutic manipulation of the annexin/Dectin-1/NOX-2 signalling axis, thus, provides a new immunological checkpoint system which can be targeted using an annexin-coated particle of the present invention, for example for use in the treatment of an autoimmune diseases.

Example 8: Dectin-1 Mediates Immunosuppressive Effects of ACs and Annexins

Externalization of annexins on apoptotic cells is critically involved in the induction of a tolerogenic DC phenotype and the development of peripheral tolerance. This immunosuppressive effect of apoptotic cells or annexins on DCs manifests itself i.a. in reduced responsiveness to Toll-like receptor (TLR)-stimulation. Accordingly, the involvement of Dectin-1 in the immunosuppressive effects of apoptotic cells or of the annexin core domain was tested.

A total of 1×10⁵ BMDCs or MM6 cells were incubated with recombinant protein (100-1000 nM), DZ, apoptotic Jurkat T-cells (0.1-4×10⁵ cells) or apoptotic RMA cells (1-4×10⁵ cells) under the presence of LPS neutralizing agent PmxB (50 µg/ml final concentration) for 4-8 h. Cells were subsequently stimulated with CpG 1668 (Invivogen; BMDCs) or R848 (Invivogen; MM6 cells). Cytokine concentrations in the supernatants were analyzed by ELISA 16-24 h after TLR stimulation. CD80 surface expression was measured 2-3 d after TLR stimulation. If not stated otherwise: The suppression of cytokine secretion or CD80 expression is normalized to CpG-stimulation only minus untreated (100−((treated−untreated)/(CpG only−untreated)) *100).

Apoptotic cells and annexin A1ΔN exerted a strong immunosuppressive effect on Dectin-1 expressing cells demonstrated by almost complete reduction (=suppression) of TLR-induced pro-inflammatory cytokine levels (FIG. 5a). In contrast, Dectin-1 KO cells were significantly less inhibited by annexin A1ΔN and human as well as murine apoptotic cells (FIG. 5a-g and FIG. 11a-c). Moreover, suppression of the co-stimulatory DC surface marker CD80 was significantly reduced in Dectin-1 KO cells. Conclusively, these data outline a role of Dectin-1 as an immunosuppressive receptor in response to apoptotic cells and the annexin core domain.

Example 9: Effective Immunosuppression of AC and Annexins Requires ROS

The annexin-mediated ROS production was detected to be abrogated by pre-treatment with gp91-TAT, confirming that NOX-2 is the main enzyme that produces ROS after annexin incubation. NOX-2 plays a role in antimicrobial defense NOX-2, in anti-inflammatory processes as well as in prevention of autoimmune diseases. It was thus investigated whether annexin-induced immunosuppression is dependent on induction of ROS. Indeed, the ROS-scavenger catalase reduced the suppressive effects of ACs and annexin compared to control-treated cells (FIG. 12). Accordingly, the suppressive effects of ACs as well as annexins were significantly reduced in functional experiments using gp91-TAT and the NOX-2-specific small molecule inhibitor GSK2795039. Finally, the functional relationship between NOX-2-dependent ROS-production and immunosuppression was confirmed using $gp91^{phox(-/-)}$-deficient BMDCs. The data clearly show the relevance of NOX-2-induced ROS in Dectin-1-mediated immunosuppression in response to the annexin core domain and ACs. Furthermore, the herein disclosed molecular mechanism of annexin-mediated immunosuppression provides a novel rationale for the role of NOX-2 in prevention of hyper-inflammatory immune responses and autoimmune diseases.

Example 10: Dectin-1 KO Mice Show Age-Related Symptoms of Autoimmunity

The in vitro results presented in the previous examples delineate an immuno-regulatory molecular pathway initiated by annexin, which activates Dectin-1 and leads to DC-inhibition via phosphorylation of SYK and NOX-2-dependent ROS release. Accordingly, deficiency in either of these components is likely to result in an autoimmune phenotype. Regarding NOX-2, it is well documented that mutations in members of the NOX-2 complex are responsible for a diverse set of autoimmune disorders, e.g. rheumatoid arthritis or lupus erythematosus. However, Dectin-1-deficient mice have not been described to develop an overt autoimmune phenotype. The present inventors reasoned that autoimmune symptoms related to loss of Dectin-1 might accumulate with age and investigated immune parameters in aged mice (77 weeks). Signs of hyper-inflammation in Dectin-1 KO mice due to a lack of sufficient DC and macrophage suppression during homeostatic turn-over of engulfed ACs were evaluated. Aged Dectin-1 KO mice showed severely enlarged spleens compared to wildtype (WT) littermates (FIG. 6a). Moreover, DCs and macrophages in spleens of aged Dectin-1 KO mice displayed an activated phenotype as analysed by CD80 and CD86 (co)-expression. Importantly, the activated cellular phenotype in aged Dectin-1 KO mice was accompanied by a higher titre of auto-antibodies (IgM & IgG isotype) against double-stranded DNA (FIG. 6b-i). Taken together, the autoimmune symptoms prevalent in aged Dectin-1 KO mice clearly indicate the involvement of Dectin-1 in homeostatic immune-regulation. Furthermore, the autoimmune phenotype in vivo supported by the in vitro studies reveals a role for Dectin-1 in uptake and immunosuppression after engagement with apoptotic cells under steady state conditions preventing the development of immune hyper-activation and autoimmunity.

In fact, while spleens of old WT littermates differed only marginally from weights of young mice of either genotype, spleens of old Dectin-1 KO mice presented with enlarged spleens, which showed up to two-fold increase in splenic weight. Moreover, an activated immune phenotype in aged Dectin-1 KO mice became also evident from the analysis of activation markers on splenic DCs and macrophages, which were significantly upregulated. Importantly, these signs of immune activation in aged Dectin-1 KO mice were accompanied by elevated titres of anti-dsDNA auto-antibodies. While all aged mice developed a titre of anti-dsDNA antibodies of the IgM isotype, only in aged Dectin-1 KO mice an isotype switch towards anti-dsDNA IgG antibodies was observed, known to be closely correlated with disease onset and severity of autoimmune disorders such as systemic lupus erythematosus.

REFERENCES

[1] Morelli A. E. and Thomson A. W. (2007) Tolerogenic dendritic cells and the quest for transplant tolerance. *Nat Rev Immunol.* 7(8):610-21. Epub 2007 Jul. 13.
[2] Mueller D. L. (2010) Mechanisms maintaining peripheral tolerance. *Nat. Immunol.* 11: 21-27.
[3] Weyd, H. et al. (2013) Annexin A1 on the surface of early apoptotic cells suppresses CD8+ T cell immunity. *PloS one.* 8, e62449.
[4] Linke B. et al. (2015) The tolerogenic function of annexins on apoptotic cells is mediated by the annexin core domain. *J Immunol.* 194(11), 5233-42.
[5] Walther, A., K. Riehemann, and V. Gerke. 2000. A novel ligand of the formyl peptide receptor: annexin I regulates neutrophil extravasation by interacting with the FPR. *Mol Cell* 5: 831-840.
[6] Brown G. D., Willment J. A. and Whitehead L. (2018) C-type lectins in immunity and homeostasis. *Nat Rev Immunol.* 18(6):374-389.
[7] Dillon S. R. (2000) Annexin V binds to viable B cells and colocalizes with a marker of lipid rafts upon B cell receptor activation. J Immunol 164: 1322-1332.
[8] Ran S. et al. (2002) Phosphatidylserine is a marker of tumor vasculature and a potential target for cancer imaging and therapy. Int J Radiat Oncol Biol Phys. 54(5):1479-84.
[9] Garnier B. et al (2009) Annexin A5-functionalized liposomes for targeting phosphatidylserine-exposing membranes. Bioconjug Chem. 20(11):2114-22. doi: 10.1021/bc9002579.
[10] Plato, A. Willment, J. A. and Brown G. D. (2013) C-type lectin-like receptors of the dectin-1 cluster: ligands and signaling pathways. *International reviews of immunology.* 32, 134-156.
[11] Temmerman K. and Nickel W. (2009) A novel flow cytometric assay to quantify interactions between proteins and membrane lipids. Journal of lipid research. 50 (6), 1245-1254. DOI: 10.1194/jlr.D800043-JLR200.

The features of the present invention disclosed in the specification, the claims, and/or in the accompanying figures may, both separately and in any combination thereof, be material for realizing the invention in various forms thereof.

The invention claimed is:
1. An annexin-coated particle, comprising a negatively charged phospholipid and annexin non-covalently coupled thereto, wherein the particle is a lipid vesicle; and the annexin is a receptor-binding annexin core domain.

2. The annexin-coated particle according to claim 1, wherein said annexin is any member of the group of an annexin A1, A5, and A13 core domain.

3. The annexin-coated particle according to claim 1, wherein said negatively charged phospholipid is any of phosphatidylserine, phosphatidylglycerol, phosphatidic acid, phosphatidylinositol, phosphatidylinositol phosphate, phosphatidylinositol biphosphate, phosphatidylinositol triphosphate, 1,2-dimyristoyl-sn-glycero-3-phosphoglycerol sodium salt (DMPG), 1,2-dimyristoyl-sn-glycero-3-phospho-L-serine sodium salt (DMPS), and 1,2-dimyristoyl-sn-glycero-3-phosphate monosodium salt (1,2-DPPA).

4. The annexin-coated particle according to claim 1, wherein said particle incorporates said negatively charged phospholipid in a particle main body and is covered with said negatively charged phospholipid.

5. The annexin-coated particle according to claim 1, wherein said particle further comprises cholesterol, PEG, a therapeutic agent other than annexin, or an antigen.

6. The annexin-coated particle according to claim 1, wherein said particle is selected from a lipid vesicle, a micelle, a solid-lipid particle, a polymeric particle, a polysaccharide particle, an iron oxide particle, a dendrimer, a viral-based particle, a DNA-based particle, a modified cell, an artificial cell, and a carbon nanotube.

7. The annexin-coated particle according to claim 6, wherein said particle is a unilamellar or multilamellar lipid vesicle.

8. The annexin-coated particle according to claim 1, wherein said particle is capable of binding to Dectin-1, DC-SIGN, Lrpl, Complement receptor 3 (ITGAM, CD11b), a formyl peptide receptor (FPR), or a lipoxin receptor.

9. The annexin-coated particle according to claim 8, wherein said particle is capable of binding to Dectin-1 via a binding site that is distinct from a β-glucan binding site of said Dectin-1.

10. The annexin-coated particle according to claim 8, wherein said binding has a tolerogenic effect by inducing NOX-2 dependent ROS production.

11. A composition comprising the annexin-coated particle as defined in claim 1 and a pharmaceutically acceptable carrier and/or excipient.

12. A method of preventing or treating a disease selected from a chronic inflammatory disease, an autoimmune disease, an allergy, and a cancer in a patient, comprising providing an effective amount of the annexin-coated particle as defined in claim 1 to said patient.

13. A method of preparing the annexin-coated particle according to claim 1, wherein said method comprises coating a lipid vesicle particle comprising a negatively charged phospholipid with an annexin, wherein the annexin is a receptor-binding annexin core domain.

14. The method according to claim 13, wherein said method comprises the following steps:
 a) Providing a phospholipid preparation comprising at least said negatively charged phospholipid, and drying said phospholipid preparation,
 b) Dissolving the dried phospholipid preparation obtained in step a) in an aqueous solution,
 c) Optionally, subjecting the solution comprising phospholipids obtain in step b) to at least one freeze/thaw-cycle,
 d) Extruding the solution comprising phospholipids obtained in step b), or optionally obtained in step c), using an extruder, and thereby obtaining a particle,
 e) Supplementing the particle obtained in step d) with an annexin, and optionally calcium, allowing said annexin to non-covalently couple to said particle, and thereby obtaining an annexin-coated particle, and
 adding an antigen and/or a therapeutic agent to the particle.

* * * * *